US008795369B1

(12) United States Patent
Pimenta et al.

(10) Patent No.: US 8,795,369 B1
(45) Date of Patent: Aug. 5, 2014

(54) FRACTURE REDUCTION DEVICE AND METHODS

(75) Inventors: Luiz Pimenta, São Paulo (BR); Lukas Eisermann, San Diego, CA (US); Matthew Copp, San Diego, CA (US); Andrew Leither, Akron, OH (US)

(73) Assignee: NuVasive, Inc., San Diego, CA (US)

( * ) Notice: Subject to any disclaimer, the term of this patent is extended or adjusted under 35 U.S.C. 154(b) by 92 days.

(21) Appl. No.: 13/184,574

(22) Filed: Jul. 18, 2011

Related U.S. Application Data

(60) Provisional application No. 61/365,108, filed on Jul. 16, 2010, provisional application No. 61/365,122, filed on Jul. 16, 2010.

(51) Int. Cl.
*A61F 2/44* (2006.01)

(52) U.S. Cl.
USPC .................. 623/17.11; 606/99; 606/86 A

(58) Field of Classification Search
USPC ....... 623/17.11–17.16; 606/86 A, 86 B, 86 R, 606/79, 87, 90, 99, 100, 105, 914, 246–249
See application file for complete search history.

(56) References Cited

U.S. PATENT DOCUMENTS

| | | | |
|---|---|---|---|
| 4,969,888 A | 11/1990 | Scholten et al. | |
| 5,827,289 A | 10/1998 | Reiley et al. | |
| 6,213,672 B1 | 4/2001 | Varga | |
| 6,241,734 B1 | 6/2001 | Scribner et al. | |
| 6,248,110 B1 | 6/2001 | Reiley et al. | |
| 6,280,456 B1 | 8/2001 | Scribner et al. | |
| 6,562,074 B2 | 5/2003 | Gerbec et al. | |
| 6,740,093 B2 | 5/2004 | Hochschuler et al. | |
| 6,852,129 B2 * | 2/2005 | Gerbec et al. | 623/17.15 |
| 6,863,673 B2 | 3/2005 | Gerbec et al. | |
| 6,981,981 B2 | 1/2006 | Reiley et al. | |
| 7,044,954 B2 | 5/2006 | Reiley et al. | |
| 7,114,501 B2 | 10/2006 | Johnson et al. | |
| 7,153,306 B2 | 12/2006 | Ralph et al. | |
| 7,166,121 B2 | 1/2007 | Reiley et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 7,500,992 B2 | 3/2009 | Li | |

(Continued)

FOREIGN PATENT DOCUMENTS

| | | |
|---|---|---|
| AU | 2002323730 B2 | 9/2004 |
| CN | 2730336 Y | 10/2005 |

(Continued)

*Primary Examiner* — Matthew Lawson
*Assistant Examiner* — Si Ming Lee
(74) *Attorney, Agent, or Firm* — NuVasive, Inc.; Jonathan Spangler; Jennifer Russell

(57) ABSTRACT

A fracture reduction implant for treating a vertebral compression fracture and instruments and methods for implanting the fracture reduction device utilizing a minimally invasive lateral approach are described. The implant may be inserted into a fractured vertebra through a T-shaped cut formed in the vertebral wall. The T-shaped cut may be formed in the lateral aspect of the wall. After insertion, a portion of the implant may be elevated within the vertebral body to reduce the fracture. The implant may include a base assembly with an elevator plate and a support column. The support column may be configured for guided insertion into the base assembly. The support column may be locked to the base assembly after insertion.

15 Claims, 23 Drawing Sheets

(56) References Cited

U.S. PATENT DOCUMENTS

| | | |
|---|---|---|
| 7,615,052 B2 | 11/2009 | Serbousek |
| 7,621,952 B2 | 11/2009 | Truckai et al. |
| 7,623,902 B2 | 11/2009 | Pacheco |
| 7,666,227 B2 | 2/2010 | Schaller |
| 7,682,364 B2 | 3/2010 | Reiley et al. |
| 7,682,378 B2 | 3/2010 | Truckai et al. |
| 7,708,733 B2 | 5/2010 | Sanders et al. |
| 7,713,273 B2 | 5/2010 | Krueger et al. |
| 7,744,637 B2 | 6/2010 | Johnson et al. |
| 7,749,255 B2 | 7/2010 | Johnson et al. |
| 7,758,644 B2 | 7/2010 | Trieu |
| 7,780,734 B2 | 8/2010 | Johnson et al. |
| 7,789,912 B2 | 9/2010 | Manzi et al. |
| 7,803,188 B2 | 9/2010 | Justis et al. |
| 7,811,291 B2 | 10/2010 | Liu et al. |
| 7,875,078 B2 | 1/2011 | Wysocki et al. |
| 7,901,409 B2 | 3/2011 | Canaveral et al. |
| 7,909,873 B2 | 3/2011 | Tan-Malecki et al. |
| 7,955,339 B2 | 6/2011 | Schwardt et al. |
| 7,959,638 B2 | 6/2011 | Osorio et al. |
| 7,967,827 B2 | 6/2011 | Osorio et al. |
| 7,967,867 B2 | 6/2011 | Barreiro et al. |
| 7,972,340 B2 | 7/2011 | Sand et al. |
| 7,972,382 B2 | 7/2011 | Foley et al. |
| 7,985,228 B2 | 7/2011 | Phan et al. |
| 8,034,071 B2 | 10/2011 | Scribner et al. |
| 8,048,030 B2 | 11/2011 | McGuckin, Jr. et al. |
| 8,052,661 B2 | 11/2011 | McGuckin, Jr. et al. |
| 8,070,754 B2 | 12/2011 | Fabian et al. |
| 8,109,933 B2 | 2/2012 | Truckai et al. |
| 8,114,084 B2 | 2/2012 | Betts |
| 8,123,755 B2 * | 2/2012 | Johnson et al. .............. 606/90 |
| 2003/0050644 A1 | 3/2003 | Boucher et al. |
| 2003/0130664 A1 | 7/2003 | Boucher et al. |
| 2003/0171812 A1 | 9/2003 | Grunberg et al. |
| 2004/0087947 A1 | 5/2004 | Lim et al. |
| 2005/0119662 A1 | 6/2005 | Reiley et al. |
| 2005/0278036 A1 | 12/2005 | Leonard et al. |
| 2005/0288678 A1 | 12/2005 | Reiley et al. |
| 2006/0095138 A1 | 5/2006 | Truckai et al. |
| 2006/0122701 A1 | 6/2006 | Kiester |
| 2006/0129244 A1 | 6/2006 | Ensign |
| 2006/0155296 A1 | 7/2006 | Richter |
| 2006/0264967 A1 | 11/2006 | Ferreyro et al. |
| 2007/0032791 A1 | 2/2007 | Greenhalgh |
| 2007/0050030 A1 | 3/2007 | Kim |
| 2007/0055259 A1 | 3/2007 | Norton et al. |
| 2007/0067034 A1 | 3/2007 | Chirico et al. |
| 2007/0093822 A1 | 4/2007 | Dutoit et al. |
| 2007/0162132 A1 | 7/2007 | Messerli |
| 2007/0179611 A1 | 8/2007 | DiPoto et al. |
| 2007/0255410 A1 * | 11/2007 | Dickson et al. ............ 623/17.11 |
| 2008/0004705 A1 | 1/2008 | Rogeau et al. |
| 2008/0009877 A1 | 1/2008 | Sankaran et al. |
| 2008/0045966 A1 * | 2/2008 | Buttermann et al. ........... 606/87 |
| 2008/0051825 A1 | 2/2008 | Reiley et al. |
| 2008/0058674 A1 | 3/2008 | Jansen et al. |
| 2008/0058826 A1 | 3/2008 | Scribner et al. |
| 2008/0058855 A1 | 3/2008 | Reiley et al. |
| 2008/0065190 A1 | 3/2008 | Osorio et al. |
| 2008/0086133 A1 | 4/2008 | Kuslich et al. |
| 2008/0177387 A1 | 7/2008 | Parimore et al. |
| 2008/0234687 A1 | 9/2008 | Schaller et al. |
| 2008/0249604 A1 | 10/2008 | Donovan et al. |
| 2008/0281364 A1 | 11/2008 | Chirico et al. |
| 2008/0294167 A1 | 11/2008 | Goldin et al. |
| 2008/0300598 A1 * | 12/2008 | Barreiro et al. ............... 606/63 |
| 2009/0024217 A1 | 1/2009 | Levy et al. |
| 2009/0054934 A1 | 2/2009 | Beyar et al. |
| 2009/0076520 A1 | 3/2009 | Choi |
| 2009/0088788 A1 | 4/2009 | Mouw |
| 2009/0138043 A1 | 5/2009 | Kohm |
| 2009/0138086 A1 * | 5/2009 | Dewey ..................... 623/17.16 |
| 2009/0164016 A1 | 6/2009 | Georgy et al. |
| 2009/0204215 A1 * | 8/2009 | McClintock et al. ...... 623/17.11 |
| 2009/0240334 A1 | 9/2009 | Richelsoph |
| 2009/0247664 A1 | 10/2009 | Truckai et al. |
| 2009/0276048 A1 | 11/2009 | Chirico et al. |
| 2009/0281627 A1 | 11/2009 | Petit |
| 2009/0299282 A1 | 12/2009 | Lau et al. |
| 2009/0299373 A1 | 12/2009 | Sisken |
| 2009/0299401 A1 | 12/2009 | Tilson |
| 2009/0326538 A1 | 12/2009 | Sennett et al. |
| 2010/0023017 A1 | 1/2010 | Beyar et al. |
| 2010/0030216 A1 | 2/2010 | Arcenio |
| 2010/0030284 A1 | 2/2010 | Abt et al. |
| 2010/0036381 A1 | 2/2010 | Vanleeuwen et al. |
| 2010/0054075 A1 | 3/2010 | Valaie |
| 2010/0070049 A1 | 3/2010 | O'Donnell et al. |
| 2010/0082033 A1 | 4/2010 | Germain |
| 2010/0082036 A1 | 4/2010 | Reiley et al. |
| 2010/0082073 A1 | 4/2010 | Thramann |
| 2010/0087826 A1 | 4/2010 | Manzi et al. |
| 2010/0087828 A1 | 4/2010 | Krueger et al. |
| 2010/0100184 A1 | 4/2010 | Krueger et al. |
| 2010/0179656 A1 | 7/2010 | Theofilos et al. |
| 2010/0198225 A1 | 8/2010 | Thompson et al. |
| 2010/0217335 A1 | 8/2010 | Chirico et al. |
| 2010/0234866 A1 | 9/2010 | Arcenio et al. |
| 2010/0247478 A1 | 9/2010 | Clineff et al. |

FOREIGN PATENT DOCUMENTS

| | | |
|---|---|---|
| DE | 102008030690 A1 | 1/2010 |
| DE | 102009011561 A1 | 9/2010 |
| DE | 102009011566 A1 | 9/2010 |
| WO | WO-98-56301 A1 | 12/1998 |
| WO | WO-99-29246 A1 | 9/1999 |
| WO | WO-99-62416 A1 | 12/1999 |
| WO | WO-2007-002108 A2 | 1/2007 |
| WO | WO-2008-060277 A2 | 5/2008 |
| WO | WO-2008-097659 A2 | 8/2008 |
| WO | WO-2010-063111 A1 | 6/2010 |
| WO | WO-2010-100287 A1 | 9/2010 |

* cited by examiner

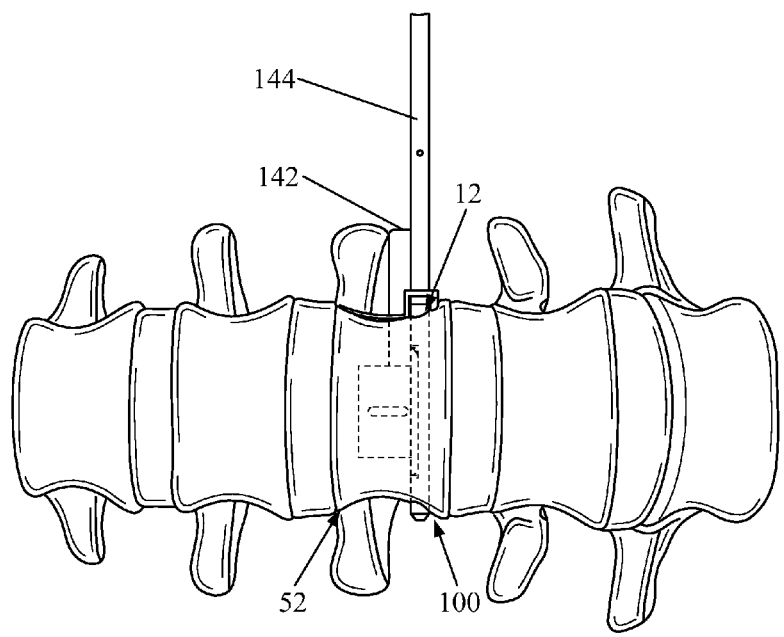
FIG. 22
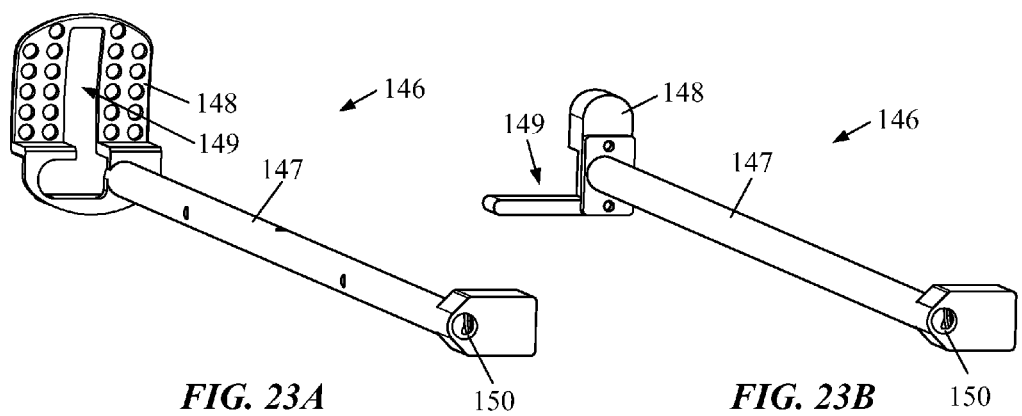
FIG. 23A     FIG. 23B

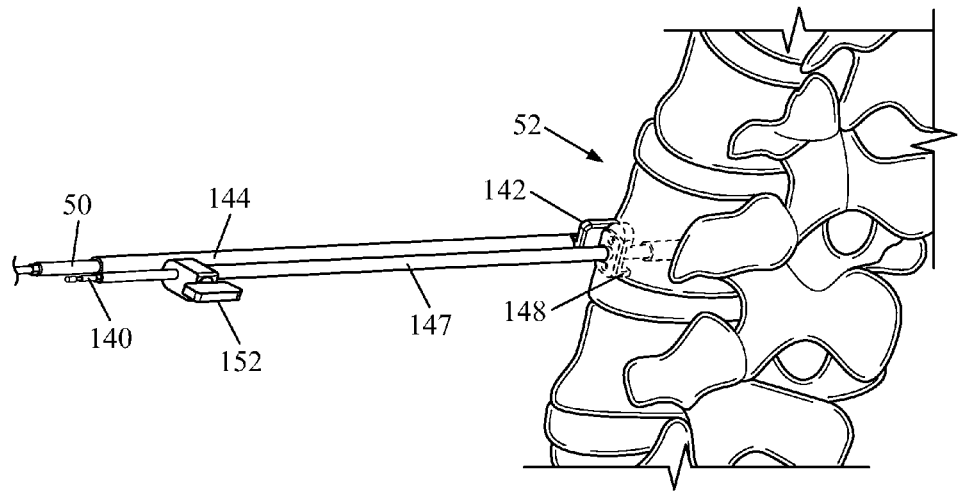
*FIG. 24*
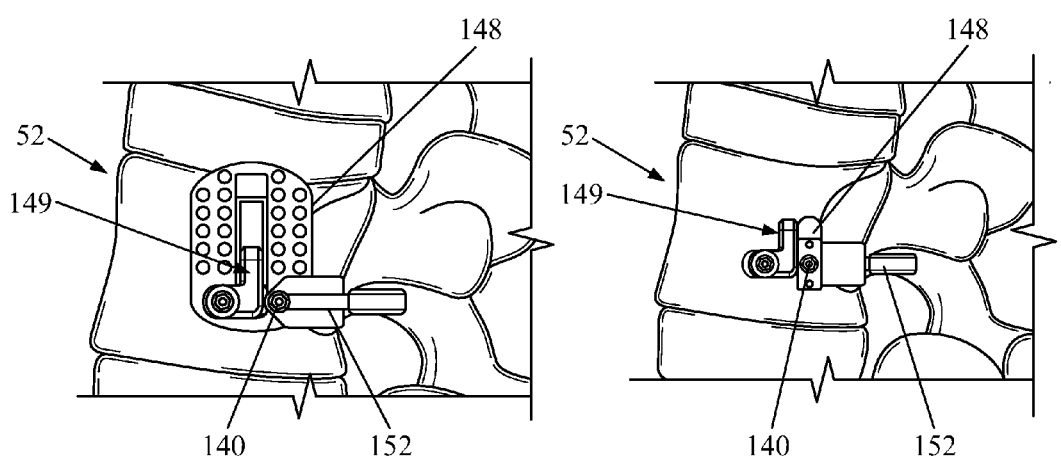
*FIG. 25A*  *FIG. 25B*

FRACTURE REDUCTION DEVICE AND METHODS

CROSS-REFERENCE TO RELATED APPLICATIONS

This application is a non-provisional patent application claiming the benefit of priority from U.S. Provisional Patent Application Ser. No. 61/365,108, filed on Jul. 16, 2010, (incorporated by reference in its entirety herein) and U.S. Provisional Patent Application Ser. No. 61/365,122, filed on Jul. 16, 2010, (incorporated by reference in its entirety herein).

FIELD

The present application describes implants, instruments, and methods for treating bone fractures of the human spine.

BACKGROUND

Vertebral compression fractures are crushing injuries to one or more vertebrae and are most commonly associated with osteoporosis. Bones weakened by osteoporosis can collapse and the resulting decrease in vertebral body height can lead to back pain, development of neurological conditions, or exacerbation of preexisting neurologic conditions. Trauma and metastatic cancer are also causes of vertebral compression fractures.

Non-surgical treatment for vertebral compression fractures includes short term bed rest, analgesics, calcium and vitamin D supplements, external bracing, and other conservative measures. If non-surgical treatment does not alleviate the painful symptoms of the fracture, surgical intervention may be required. Typical compression fracture patients are elderly and often do not tolerate open surgical procedures well. For these reasons, minimally invasive surgical techniques for treating these fractures have been developed. One such technique is percutaneous vertebroplasty which involves injecting bone cement under pressure into the fractured vertebra to provide stabilization. A second technique is balloon kyphoplasty which uses two balloons that are introduced into the vertebra to reduce the fracture. The balloons are then deflated and removed, and bone cement is placed in the void. While these techniques have seen an increase in popularity, neither consistently elevates the vertebral body end plates sufficiently to fully restore lost bone height for all indications. The present invention is directed at overcoming, or at least improving upon, the disadvantages of the prior art.

SUMMARY

This application describes an implant assembly and methods for restoring bone height after a vertebral compression fracture. The implant may be used in the cervical, thoracic, and lumbar spine. According to one embodiment, the implant assembly includes a base plate, an elevator plate, and a support column. One or more locking mechanisms may also be provided. The implant components are available in multiple lengths, widths, and heights to tailor to the size requirements of each fracture.

The implant is preferably composed of a surgical-grade metal material, including, but not necessarily limited to, titanium, stainless steel, and cobalt chrome. Alternatively, the implant may be composed of a carbon fiber reinforced plastic (CFRP), epoxy, polyester, vinyl ester, nylon, or poly-ether-ether-ketone (PEEK), and/or ceramic-reinforced PEEK, alone or in combination with a surgical-grade metal material.

When implanting within the lumbar and thoracic spine, access to the operative site is accomplished via a lateral approach. In the lumber spine, the approach is preferably a neurophysiology-guided transpsoas approach in the lumbar spine. This approach provides a large access window to permit introduction of a robust implant better suited for fully restoring the vertebral height while still achieving advantages of a minimally invasive approach such that it is generally well tolerated by elderly patients. According to one example, the neurophysiology guided trans-psoas approach to the lumbar spine is performed as follows. The skin is incised at the appropriate lateral location. Blunt finger dissection through the muscle layers allows safe access into the retroperitoneal space. The finger is used to guide an initial instrument to the surface of the psoas muscle through the retroperitoneal space. Once the initial instrument is safely guided to the surface of the psoas muscle, it is attached to a neurophysiologic monitoring system which is used to guide the direction of the approach away from nearby nerves. Using neurophysiologic guidance, the initial instrument is gently advanced through the psoas muscle. The neurophysiologic monitoring system confirms location of nerves near the distal end of the instrument. Fluoroscopy may be used simultaneously to assure correct targeting of the vertebral fracture. Once the instrument is docked on the target vertebra in the desired position, the position is secured with a k-wire. An operative corridor is thereafter created using a series of sequential dilators and a retractor assembly.

Following creation of the operative corridor, a cavity is created in the vertebral body to receive the implant. The cavity is upside down T-shaped and may be created using a single box T-shaped cutter, or, using separate horizontal and vertical cutters (among other options). Multiple tamp-sizers can be used to dilate the T-shaped cut to the appropriate size, if necessary. As the T-shaped cut is formed, cancellous bone is impacted outwards toward the cortical bone. Once the cavity is formed an implant may be inserted. The implant may include a base assembly with an elevator plate and support column. An appropriately sized base assembly is selected based on the size requirements of the patient. The base assembly is introduced into the vertebral body through the T-shaped cut. Insertion of the implant may be guided by a guide rod. The implant is advanced all the way across the vertebral space and positioned so that there is a small overhang over the cortical, lateral aspects of the vertebral body to help stabilize the implant and prevent subsidence in the softer cancellous bone.

The elevator plate is raised from the base plate using multiple distraction shims. The use of multiple distraction shims includes, inserting a small shim which distracts the elevator plate a certain height, removing the small shim and then repeating this process with progressively larger shims until the desired height is reached. Once the elevator plate is elevated to the final height and the vertebral fracture is fully reduced, the final distraction shim is removed. The support column is inserted into the base assembly through a slotted passageway in the support strut. The support column is then locked to the base plate. After implant placement, bone growth material may be used to fill the voids in the vertebra. Following successful implantation, the retractor assembly and all of the surgical instruments are removed and the operative corridor is closed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 22 is an anterior view of a spine showing the base assembly with attached rod extensions and elevator retainer positioned in a target vertebral body;

FIG. 23A is a perspective view of a blocker, according to a first example embodiment;

FIG. 23 B is a perspective view of a blocker, according to a second example embodiment;

FIG. 24 is an antero-lateral view of the spine of FIG. 22 with a blocker advanced over one of the rod extensions and contacting the exterior of the vertebral body;

FIG. 25A is a lateral view of the blocker of FIG. 23A positioned adjacent to the target vertebral body;

FIG. 25B is a lateral view of the blocker of FIG. 23B positioned adjacent to the target vertebral body;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The vertebral compression fracture reduction implant and methods for use disclosed herein boasts a variety of inventive features and components that warrant patent protection, both individually and in combination.

Figure 1:
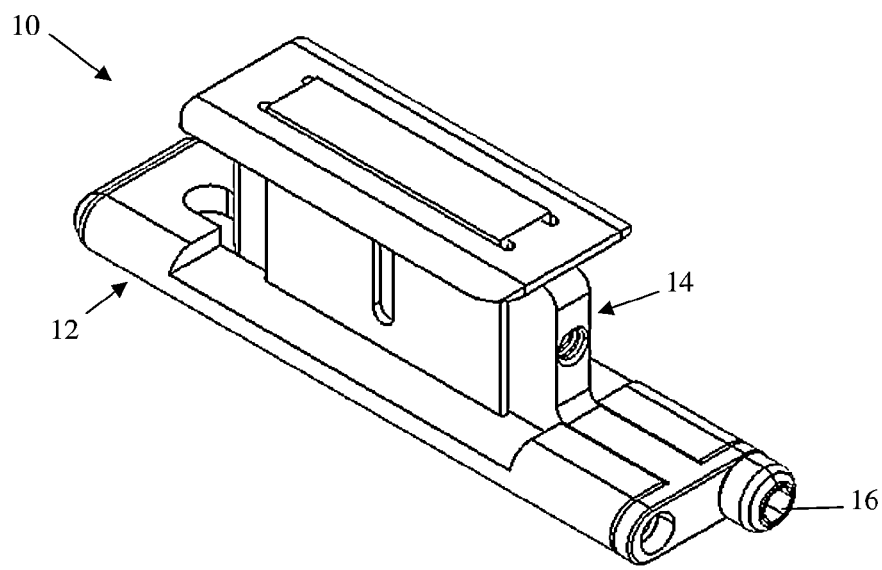
FIG. 1 is a perspective view of a fracture reduction implant assembly for treatment of a vertebral compression, the implant assembly including a base assembly and a support column, according to one example embodiment.
Figure 2:
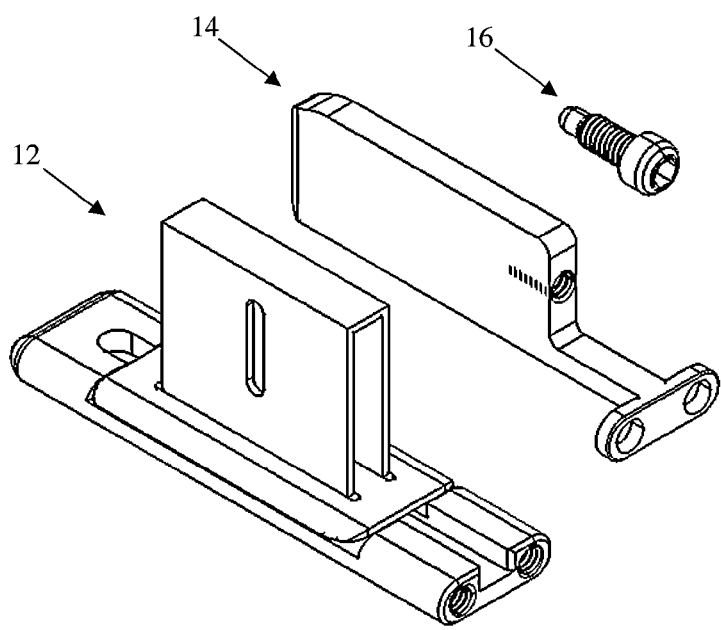
FIG. 2 is an exploded view of the implant assembly of FIG. 1.

FIGS. 1-2 illustrate one example embodiment of a fracture reduction implant 10 for treating a vertebral fracture. In use the implant 10 is inserted into a cavity formed in the fractured (target) vertebral body where it is expanded to restore the height of the vertebra and prevent recollapse in the future. The implant is optimized for insertion from a lateral access approach to the spine. The implant 10 may be used in any of the cervical, thoracic, and lumbar spine and may be sized accordingly. The implant 10 includes a base assembly 12 and a support column 14. A lock, for example, the locking screw 16 may also be provided to lock the support column 14 to the base assembly 12.

Figure 3:
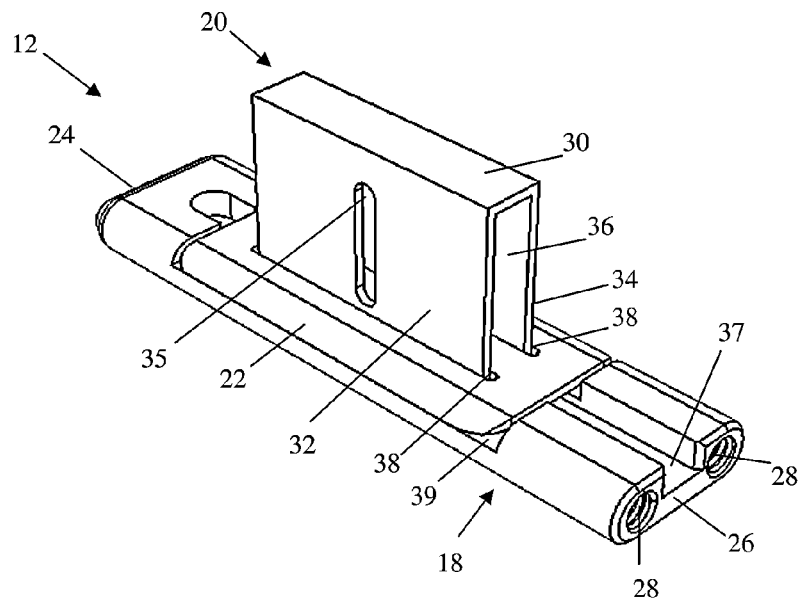
FIG. 3 is a perspective view of the base assembly of FIG. 1.

As illustrated in FIG. 3, the base assembly 12 includes a base plate 18, a support strut 20 extending generally perpendicularly from the base plate 18, and an elevator plate 22. The base plate 18 has (by way of example) a generally rectangular footprint dimensioned to allow positioning across the vertebral body from a lateral insertion approach. The length of the base plate 18 extends from a distal or leading end 24 to a proximal or trailing end 26. The length of the base plate 18 is preferably such that the base plate 18 spans the length of the vertebral body when inserted such that the proximal end 24 and distal end 26 extends to the cortical outer wall of the vertebral body, providing a solid base for the implant 10. By way of example, the base plate 18 length may be in the range of 45 mm to 60 mm. The base plate may have a width in the range of 14 mm to 26 mm. The height of the base assembly 12, including the base plate 20 and the support strut 20, may be in the range of 12 mm to 22 mm. According to one example, multiple base assemblies according to different size configurations are provided in order to match the implant 10 to the particular patient anatomy. By way of example, base assemblies may be provided with length dimensions increasing in 5 mm increments from 45 mm to 60 mm, width dimensions of 14 mm and 18 mm, and height dimensions increasing in 2 mm increments from 12 mm to 22 mm. The support strut 20 extends from the base plate 18 and includes a includes an upper surface 30, a first side wall 32, and second side wall 34, such that a slot 36 is formed which extends from the base plate 18. The slot 36 is dimensioned to receive the support column 14 therethrough. Viewing windows 35 in the form of vertical slots are situated in the center of each of the first side wall 32 and second side wall 34. The viewing windows 35 are recognizable in an A/P (Anterior/Posterior) fluoroscopy image to aid with implant positioning during insertion. A longitudinal channel 37 extends along the upper surface of the base plate 18. The longitudinal channel 37 is aligned with the slot 36 in the support strut 20 and extends from and opening in the proximal end 26 to a position short of the distal end 24 but beyond the support strut 20. The longitudinal channel 37 has a width dimension to accommodate the support column 14 which slides into position through the longitudinal channel 37 and slot 36. The upper surface of the base plate 18 also includes a recess 39 in which the elevator plate 22 rests such that it is flush with the base plate 18 when in the fully lowered, insertion position.

The elevator plate 22 has (by way of example) a generally rectangular shape to match the rectangular shape of the base plate 18. The width of the elevator plate 22 is approximately equal to the width of the base plate 18, and, as previously indicated sits flush with the exterior surfaces of the base plate 18 by virtue of the recess 39 in which the elevator plate is received. A pair of slits 38 extend longitudinally through the interior of the elevator plate 18. The first side wall 32 and the second side wall 34 of the support strut 20 extend through the slits 38 such that the elevator plate 22 may move vertically along the support strut 20 from the base plate 18 to the upper surface 30 of the support strut 20.

Figure 4:
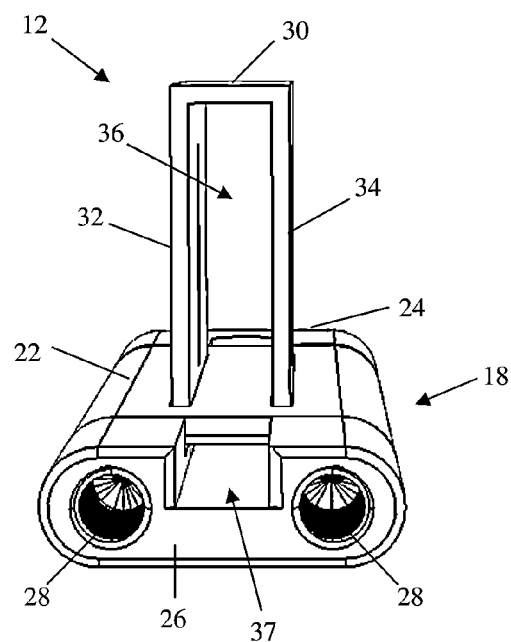
FIG. 4 is a perspective proximal view of the base assembly FIG. 1.
Figure 20:
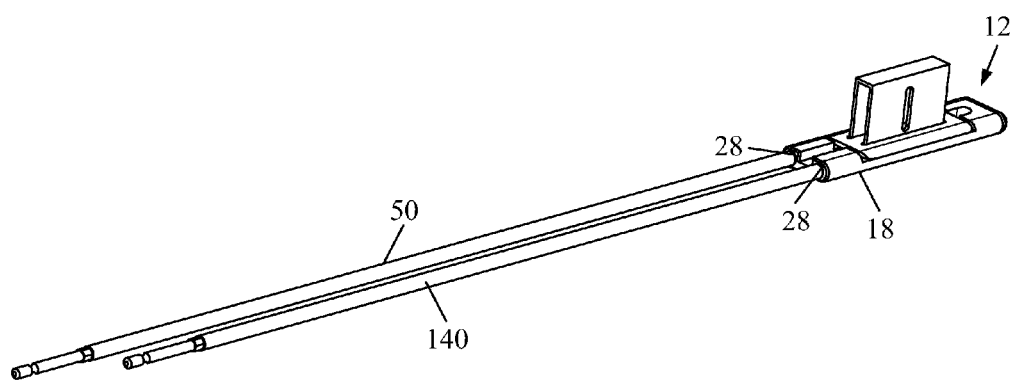
FIG. 20 is a perspective view of the base assembly of FIG. 3 with a pair of rod extensions coupled to base assembly.

FIG. 4 illustrates the proximal end 26 of base plate 18 which includes two receptacles 28. The receptacles 28 are configured for removable coupling with instruments used to facilitate insertion of the implant 10, including, for example, a guide rod 50 and blocker rod 140 (FIG. 20). Receptacles 28 are also each configured such that they can receive and engage a lock screw 16. The lock screws 16 may be used to lock the support t column 14 to the base assembly 12.

Figure 5:
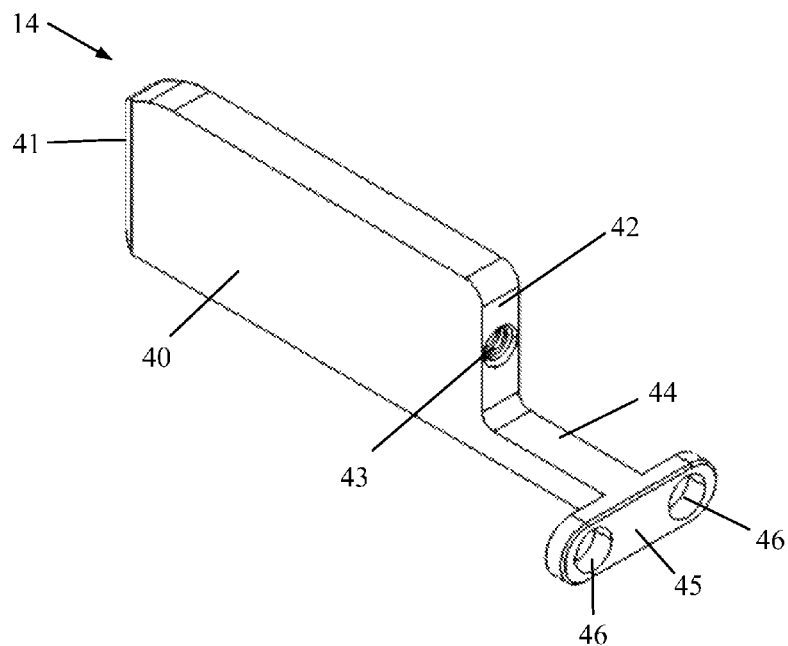
FIG. 5 is a perspective view of the support column of FIG. 1.
Figure 6:
FIG. 6 is a side view of the support column of FIG. 1, coupled to a support column inserter.
Figure 19:
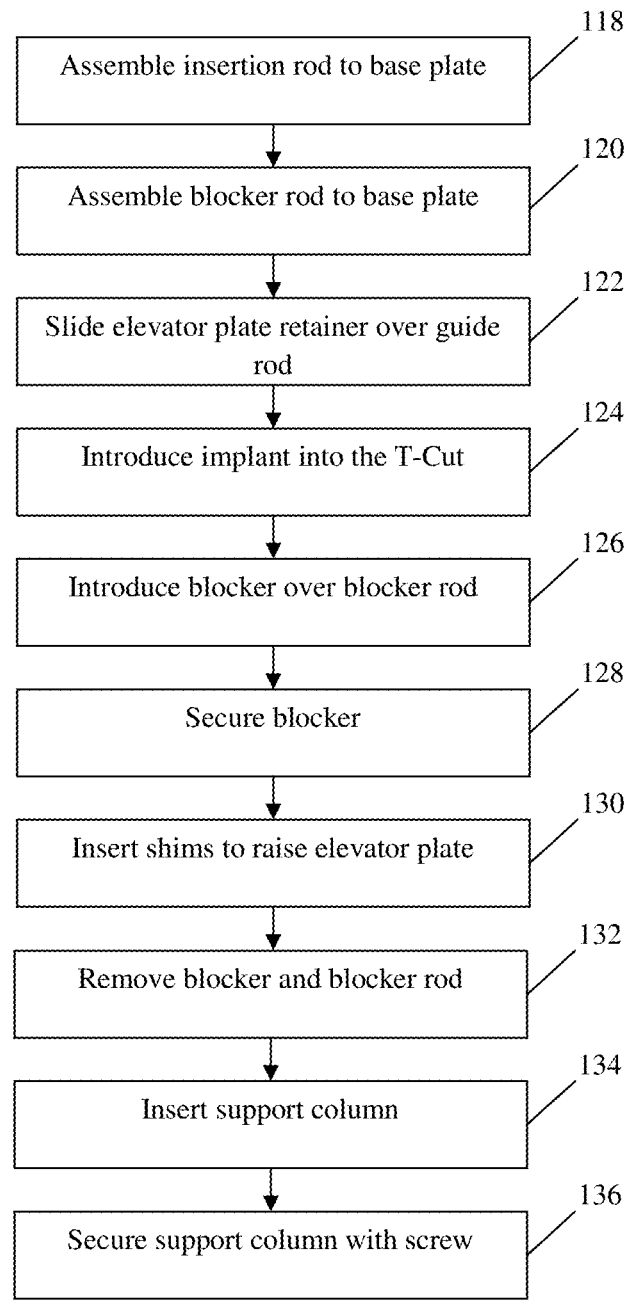
FIG. 19 is a flowchart outlining the steps according to one example method for implanting the implant assembly of FIG. 1 in order to reduce a vertebral compression fracture.
Figure 35:
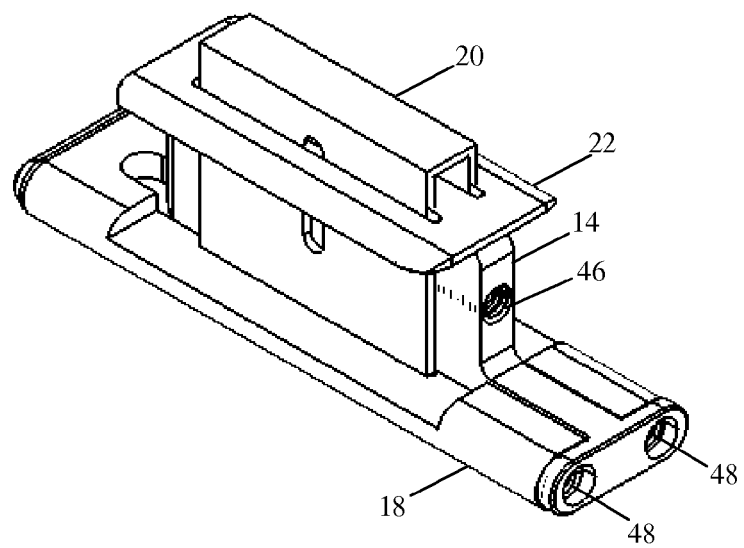
FIG. 35 is a perspective view of the implant assembly of FIG. 1 with the support column fully inserted.
Figure 36:
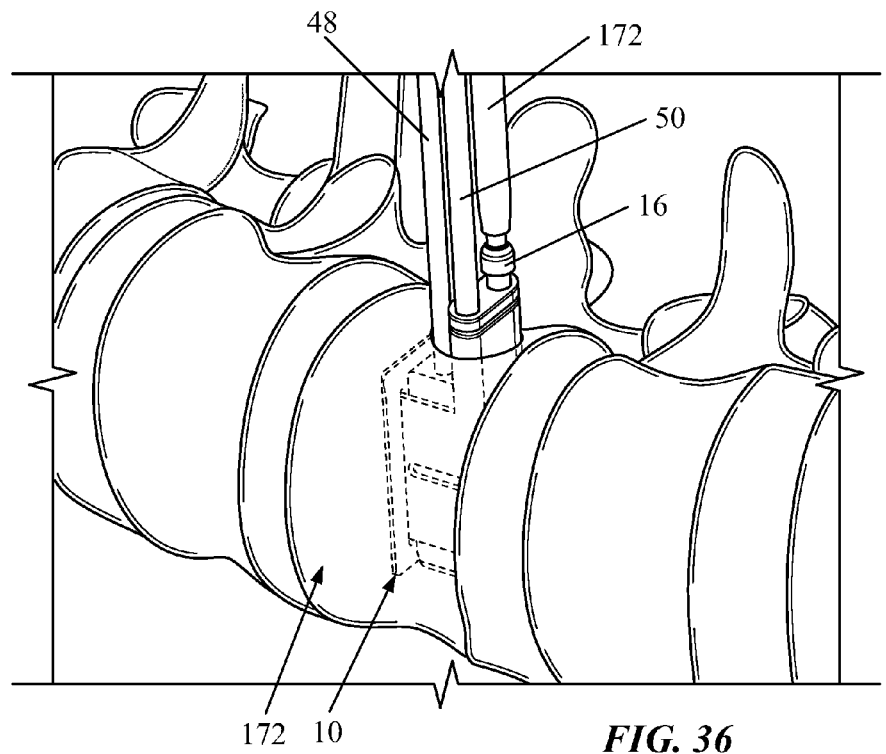
FIG. 36 is a perspective antero-lateral view of a spine with the implant assembly of FIG. 1 fully deployed in the target vertebral body and with a locking screw being engaged to lock the support column to the base assembly.
Figure 37:
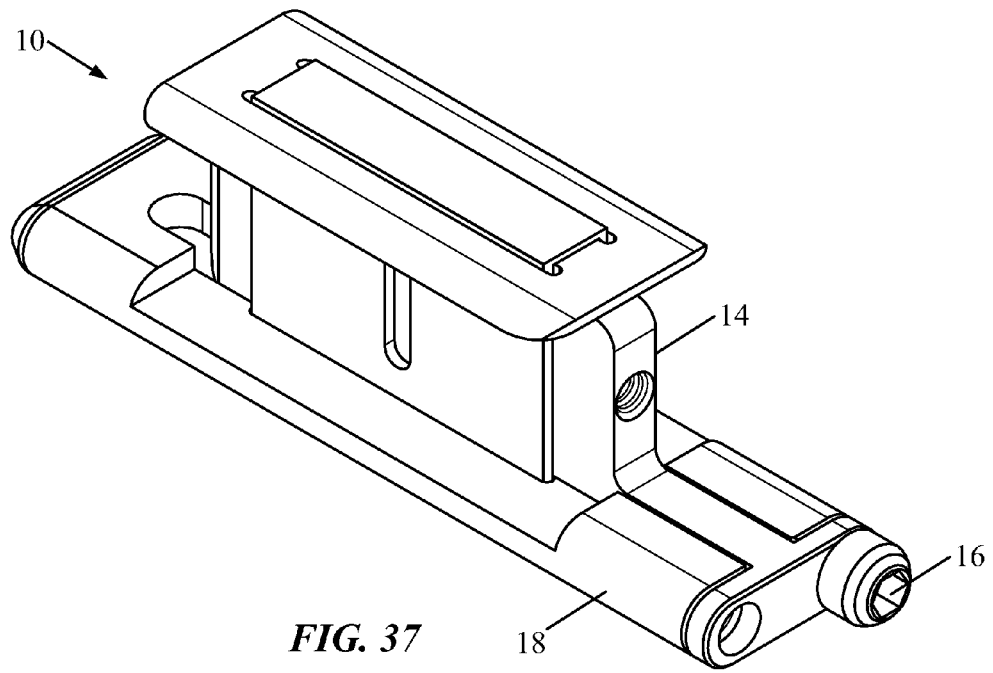
FIG. 37 is a perspective view of the implant assembly of FIG. 1, with the support column fully inserted and affixed to the base assembly with a locking screw.

With reference to FIG. 5, the support column 14 includes a body 40 having a distal end 41 and a proximal end 42, a neck 44 extending proximally from the bottom of the proximal end 42, and an elongated end face 45 situated at the end of the neck 44. The body 40 is inserted through the support strut 20, supporting and maintain the elevator plate 22 in the elevated position. The proximal end 42 of body 40 contains an insertion aperture 43 configured to threadedly couple with a support column inserter 55, as illustrated in FIG. 6. The length of the body 40 matches approximately the length of the elevator plate 22 and the length of the neck is matches approximately the length of the base plate 18 from the proximal end 26 to the start of the elevator plate 18 such that when the support column 14 is fully inserted, the end face 45 rests flush against the proximal end 26 of the base plate. A pair of guide holes 46 in the end face 45 align with the receptacles 28 of the base plate distal end 26 (FIG. 35). The guide holes 46 are dimensioned such that they are capable of slidably passing over various instruments, including, but not limited to the guide rod 50 and the blocking rod 140 as shown in FIG. 19. These guide holes 46 are also dimensioned to permit passage of the shaft of locking screw 16 but not the head of the locking screw 16, such that the locking screw may engage one of the base plate receptacles through a guide hole to lock the support column 14 to the base assembly 12 (FIG. 36).

Figure 7:
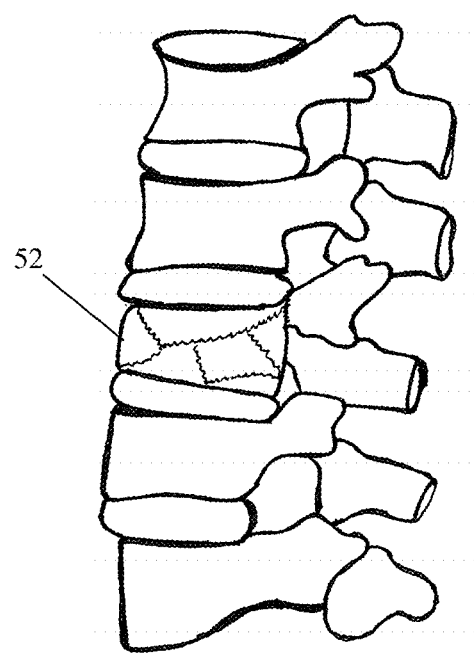
FIG. 7 is an illustration depicting a vertebral compression fracture that may be treated with the implant assembly of FIG. 1.
Figure 8:
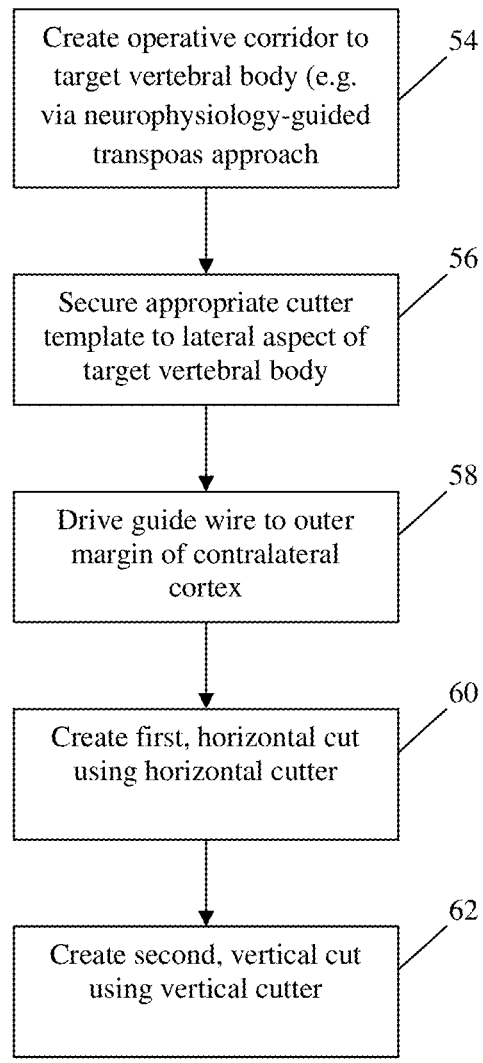
FIG. 8 is a flow chart outlining the steps according to one example method for preparing a target vertebral body for receiving the implant assembly of FIG. 1.
Figure 9:
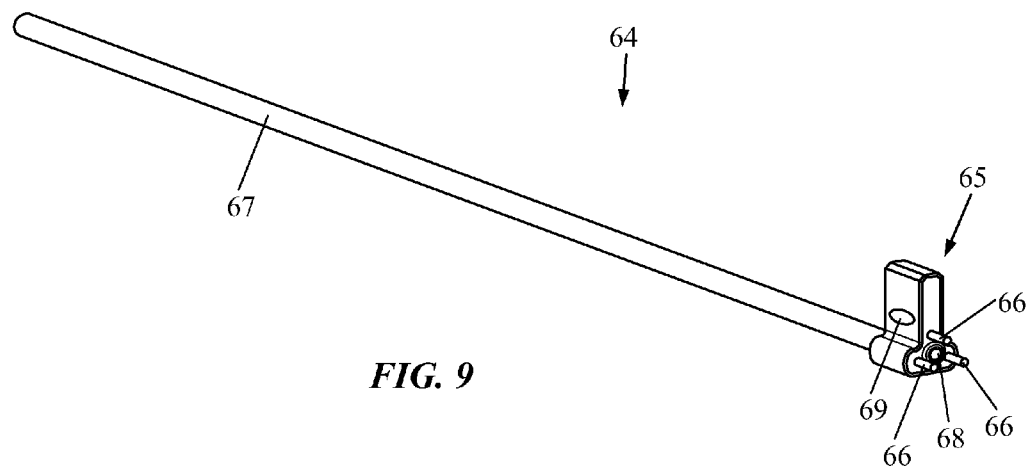
FIG. 9 is a perspective view of a cutter template used during the preparation of a fractured vertebral body to receive the implant assembly of FIG. 1.
Figure 10:
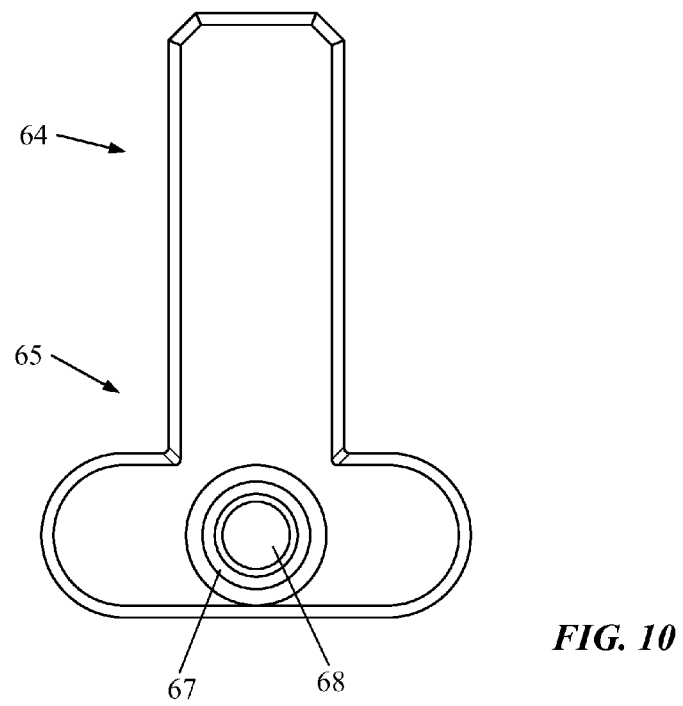
FIG. 10 is a cut-away proximal view of the cutter template of FIG. 9.
Figure 11:
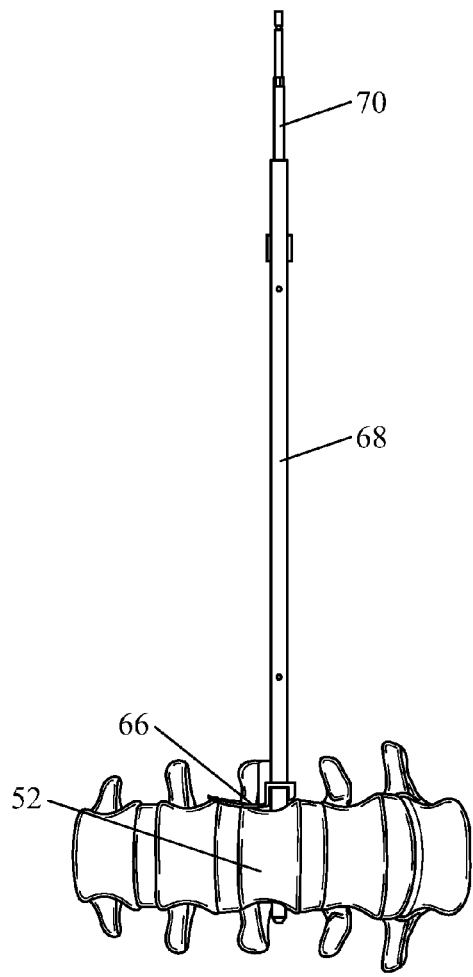
FIG. 11 is an anterior view of a spine with the cutter template secured to a lateral aspect of the a target vertebral body of the spine and a guide wire secured to the target vertebral body through the cutter template.

FIG. 7 is an illustration of a fractured vertebra 52 in the human patients spine for which the implant 10 may be deployed for treatment. FIG. 8 sets forth steps, which are depicted in FIGS. 9-18, utilized according to one example method for preparing a target vertebra 52 within the spine to receive the implant 10. At step 54, and operative corridor to the vertebral body 56 is achieved via a lateral approach (e.g. a neurophysiology-guided transpsoas approach). At step 56, a cutter template 64 corresponding to the desired width and height of the implant 10 is chosen. As shown in FIGS. 9-10, the cutter template 64 has a head 65 that matches the shape of the T-cut which is to be created in the vertebral body. The head includes at least one, and preferably 3, small securing spikes 66 extending distally from the head. The head 65 also includes a viewing slot 69 formed therethrough to help ensure proper orientation with A/P fluoroscopy. A cannulated shaft 67 extends proximally from the head 65 and connects with an aperture 68 extending through the head 65. Together, the cannulated shaft 67 and aperture 68 are configured to permit passage of a guide wire. A/P and lateral fluoroscopy views may be utilized to place the template 64 in the desired position and orientation on the target fractured vertebral body 52. Also at step 56, the template 64 is secured to the vertebral body 52 by impacting the shaft 67 to penetrate the securing spikes 66 into the vertebral body 52. Once the template 64 is secured to vertebral body 52, at step 58 a guide wire 70 may be advanced into the vertebral body through the cannulated shaft 67 (FIG. 11). The cannulated shaft guides the guide wire into the correct position and supports the guide wire to prevent excessive bending as the wire is driven into the vertebral body 52. By way of example only, the tip 72 of the guide wire 70 may be a trocar tip or a blunt tip. The guide wire 70 directs the cutter instruments and is also used to determine the width of the vertebral body 52, and hence the length of the implant 10 to be implanted.

Figure 12:
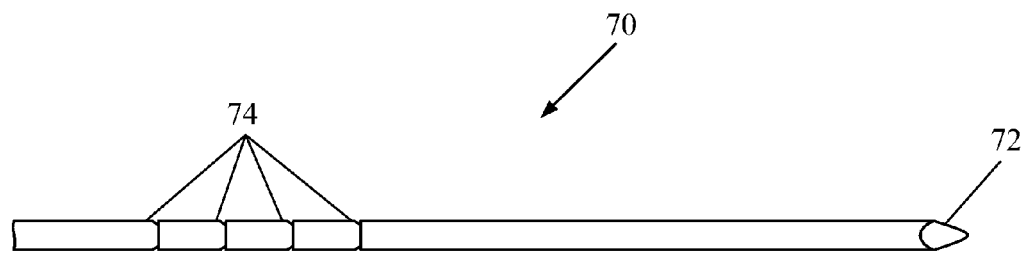
FIG. 12 is a side view of a notched guide wire, according to one example embodiment.
Figure 13:
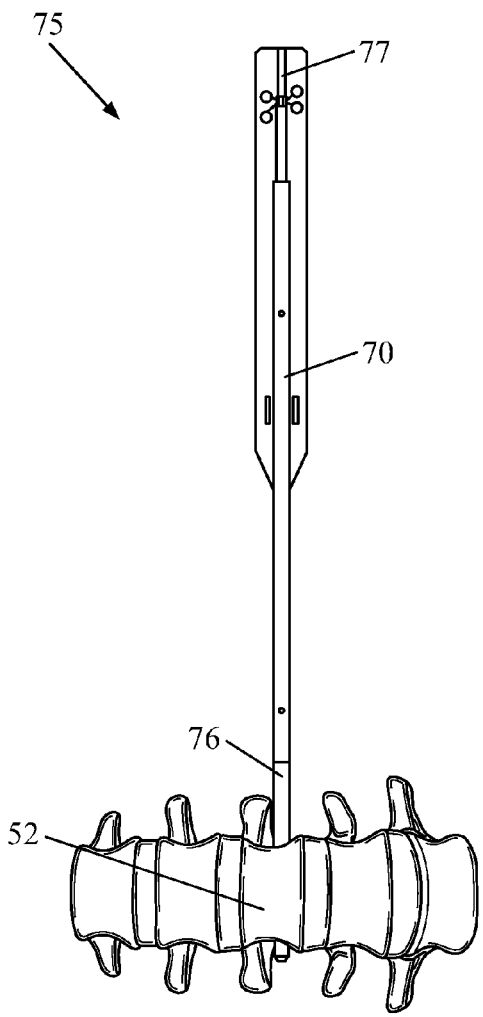
FIG. 13 is a anterior of the spine of FIG. 11 with the cutter template removed and a depth gauge deployed over the guide wire.

According to one example embodiment, shown in FIG. 12, the guide wire 70 may include notched depth markings 74 such that the depth of the guide wire 70 may be read directly off of the guide wire 70. For example, the notches may be formed at 45 mm, 50 mm, 55 mm, and 60 mm (corresponding to the implant lengths provided according to a preferred example) from the tip of the guide wire 70. Thus, with the guide wire properly advanced to the contralateral margin the appropriate length implant can be determined using A/P fluoroscopy. Alternatively, a depth gauge 75 may be used to determine the width of the vertebral body 52 (and length of the implant 10 to be implanted). As illustrated in FIG. 13, the depth gauge 75 includes a cannulated distal end 76 which can be advanced over the guide wire 70 until it rests on the vertebral body 52. The guide wire 70 extends out of the cannulated distal end 76 along a handle having depth markings 77 that correspond to the length of wire extending distally beyond the distal end 76 of the depth gauge (i.e. the length of wire penetrated into the vertebral body).

Figure 14:
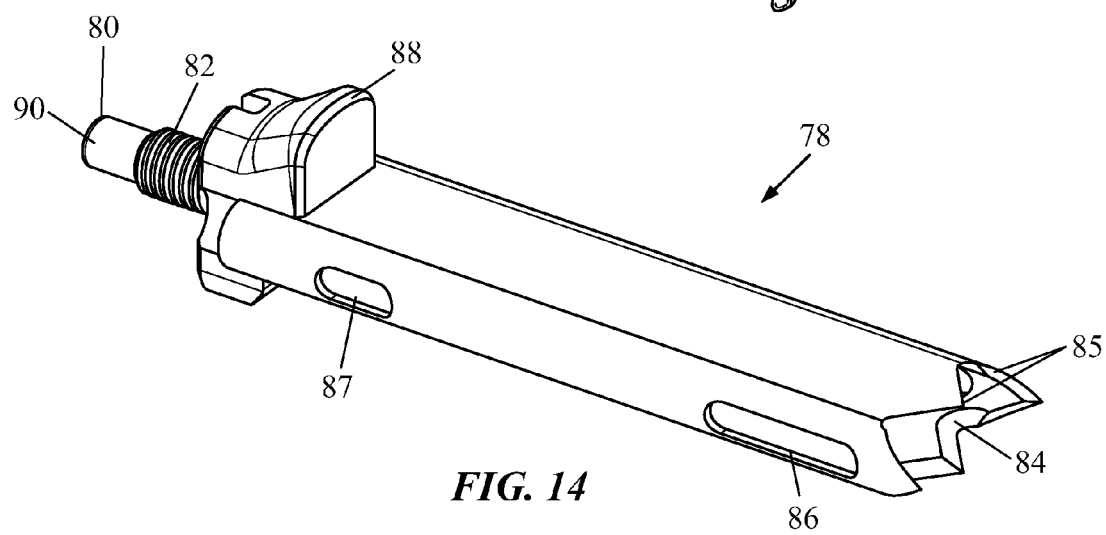
FIG. 14 is a perspective view of a horizontal cutter; according to one example embodiment.
Figure 15:
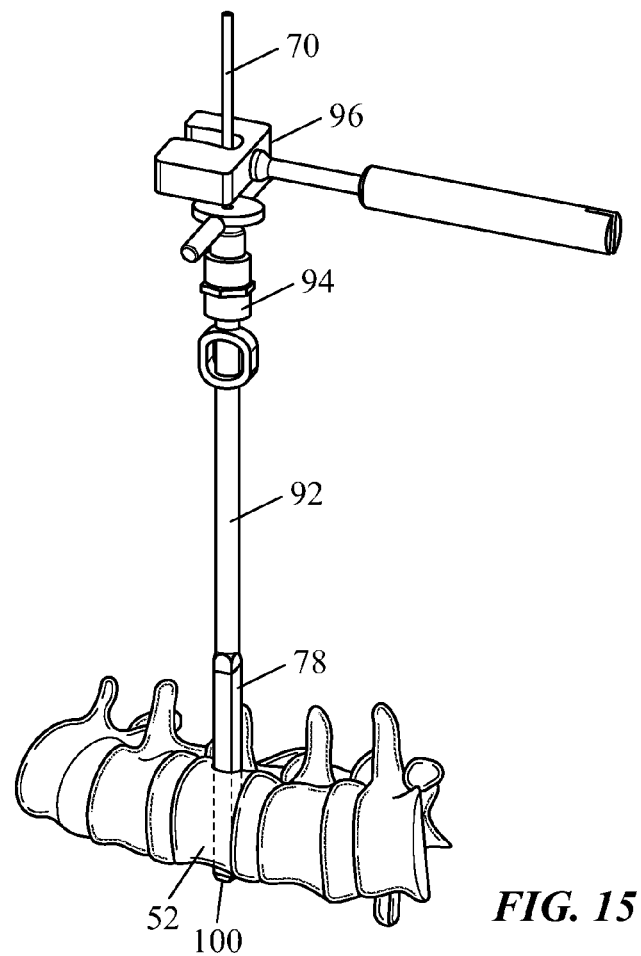
FIG. 15 is an antero-lateral view of the spine of FIG. 13 with the depth gauge removed and a horizontal cutter deployed over the guide wire.
Figure 16:
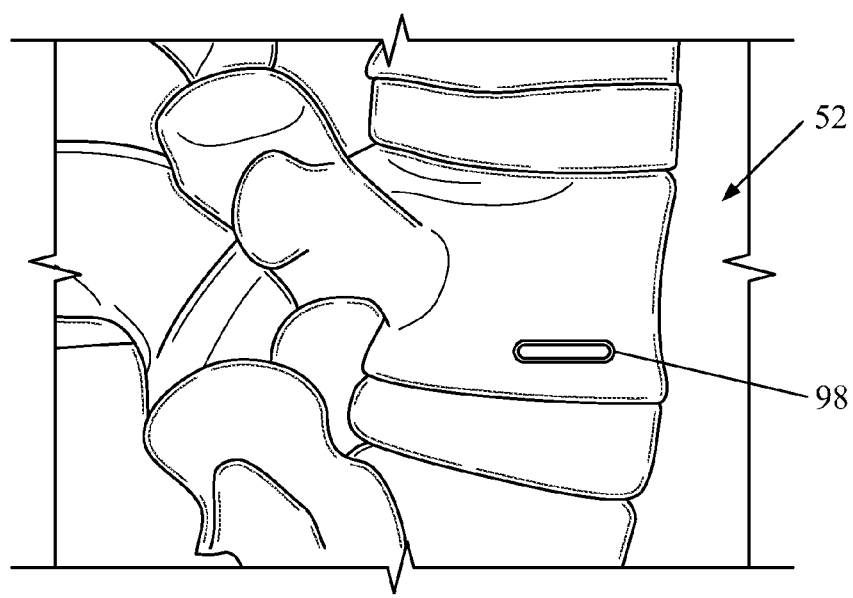
FIG. 16 is a lateral view of a spine with a horizontal cut formed by the cutter of FIG. 14 in the target vertebral body.
Figure 17:
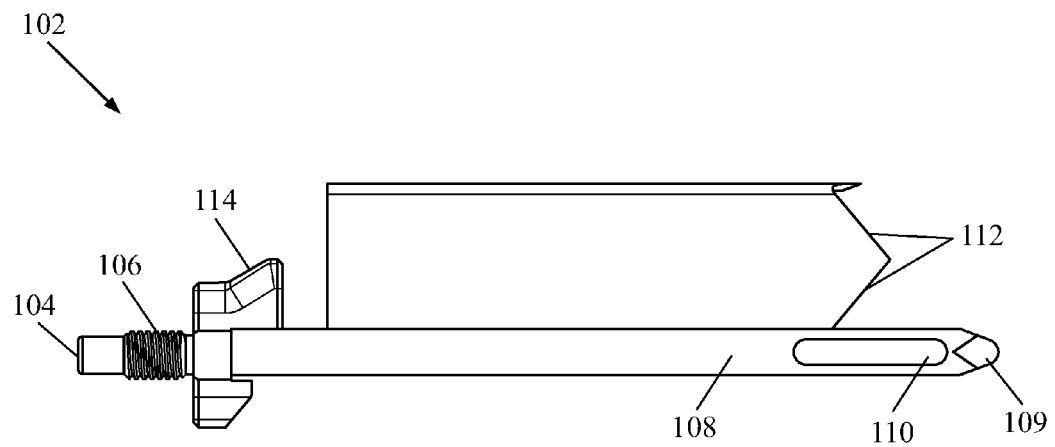
FIG. 17 is a side view of a vertical cutter according to one example embodiment.

At step 60, as highlighted in FIGS. 14-16, a first, horizontal cut 98 is made in the fractured vertebral body 52 using a horizontal cutter 78. The horizontal cutter 78 includes serrations 85 around the distal cutting end 84 for cutting through the vertebral body 52. A shoulder 88 adjacent to the proximal end 80 prevents advancement of the cutter 78 through the vertebral body into the contralateral tissues. The cutter may be provided in multiple lengths corresponding to the length options of the implant 10. A threaded member 82 at the proximal end 80 permits coupling to a handle, such as the cutter holder 92. The proximal end 80 includes a cannulated aperture 90 extending into the interior of the cutter body such that the horizontal cutter 78 may be introduced over the guide wire 70. The horizontal cutter 78 includes viewing slots, including distal viewing slot 85 and proximal viewing slot 86 that are visible under A/P fluoroscopy. The viewing slots 86 and 87 are spaced to correspond to implant length. The distal slot 86 indicates how far the cutter needs to be advanced to reach the contralateral margin of the vertebral body 52.

To facilitate advancement of the horizontal cutter 78 through the vertebral body 52, the cutter holder 92 may be further coupled to a handle outfitted with a strike plate (for example, the cannulated T-handle 94 of FIG. 15). A forked mallet 96 (or similar instrument suited for striking the T-handle 94 around the guide wire 70) may be used to drive the horizontal cutter 78 into the fractured vertebral body 52. The horizontal cutter 98 should be advanced until a horizontal cut 98 has been made through the contralateral cortical margin 100, as indicated by the distal viewing slot 86. It is to be appreciated that once the horizontal cut 98 has been started, the guide wire 70 may be removed and the horizontal cut 98 and vertical cut 116 can be finished without the guide wire 70, preventing inadvertent advancement of the guide wire 70 into the contralateral tissues. Once the desired horizontal cut 98 has been made, the horizontal cutter 78, along with the cutter holder 92 and cannulated T-handle 94, may be removed (FIG. 16).

At step 62, a second, vertical cut 116 is made through the fractured vertebral body 52 using a vertical cutter 102. The horizontal cut 98 acts as a guide for the vertical cutter 102, illustrated in FIG. 17. The vertical cutter 102 includes a sled 108, dimensioned to be received into the horizontal cut 98, with a tapered distal end 109 for easy insertion through the horizontal cut 98 as the vertical cutter 102 is advanced into the fractured vertebral body 52. The sled also includes a distal viewing slot 110 that is visible under A/P fluoroscopy. The vertical cutter 116 also includes serrated edges 112 perpendicular to the distal end 108, a shoulder 114 adjacent to the proximal end 104 for preventing inadvertent advancement into the contralateral tissues, and a threaded member 106 at the proximal or trailing end 104 for threadably receiving the cutter holder 92.

Figure 18:
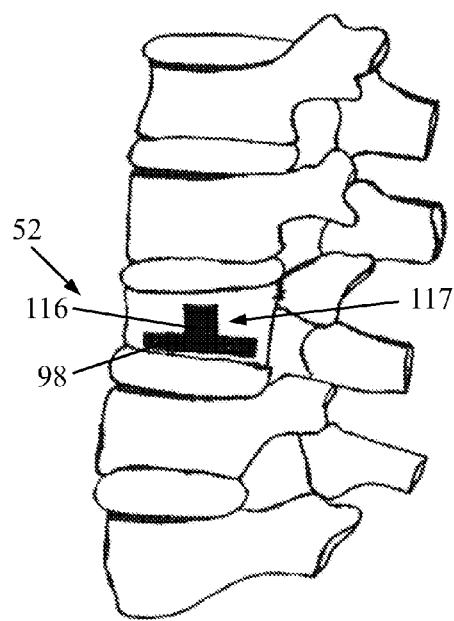
FIG. 18 is a lateral view of a spine with a vertical cut formed by the cutter of FIG. 17 connecting with the horizontal cut of FIG. 16 to make a T-cut cavity in the target vertebral body, according to one example embodiment.

The vertical cutter 102 is assembled to the cutter holder 92 via the threaded member 106 at the proximal end 104 of the vertical cutter 102. The cutter holder 92 may be further coupled to a handle outfitted with a strike plate (for example, the cannulated T-handle 94 of FIG. 15) which can be impacted to drive the cutter. The vertical cutter 102 may then be advanced through the vertebral body 52 until it has aligned with the contralateral cortical margin 100 of the vertebral body 52, as indicated by the distal viewing slot 110. Once the desired vertical cut 116 has been made, the vertical cutter 102, cutter holder 92, and cannulated T-handle 94, may be removed, leaving a T-cut cavity 117, and any remaining bony debris left inside the T-cut 117 may be removed using a small curette or other suitable surgical instrument. FIG. 18 depicts the vertebral body 52 with T-cut 117 formed there in.

Figure 21:
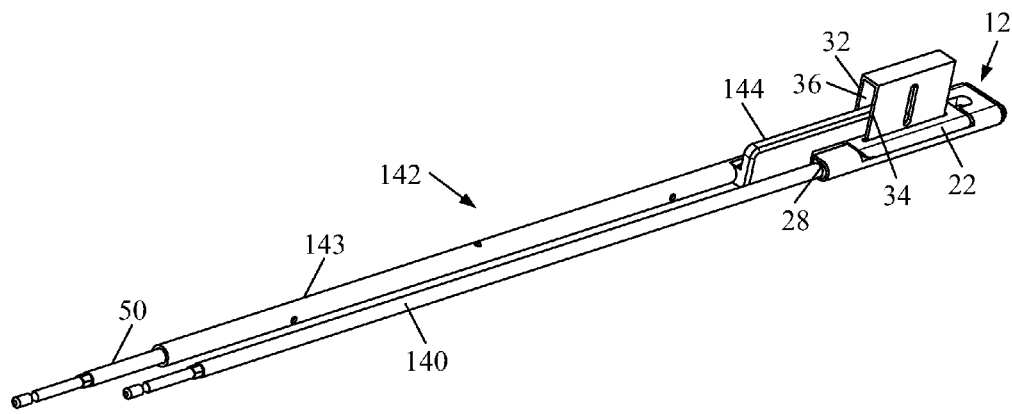
FIG. 21 is a perspective view of the base assembly of FIG. 20 with an elevator retainer inserted over one of the rod extensions.
Figure 26:
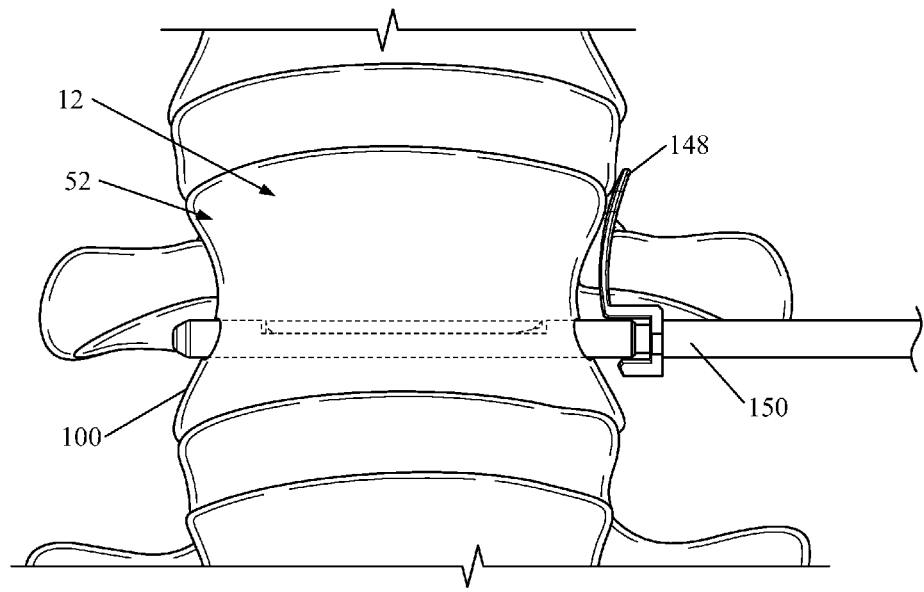
FIG. 26 is an anterior view of the spine and blocker of FIG. 25A.

FIG. 19 sets forth steps, which are depicted in FIGS. 19-36, utilized according to one example method for deploying the implant into the target vertebral body 52. As illustrated in FIG. 20, at step 118 the guide rod 50 is inserted into one receptacle 28 on the base plate 18. The guide rod 50 will be used to insert the implant into the T-cut 117 and later, as a guide for inserting distraction shims. The guide rod 50 includes a quick connect proximal end (e.g. male Hudson connector) which can be attached to a handle to aid in threading the guide rod 50 into the receptacle 28. At step 120m, the blocker rod 150 is inserted into the second receptacle 28 on the base plate 18. The blocker rod 140 will be used to guide positioning of a blocker 146 which prevents the implant 10 from advancing distally during shim insertion to elevate the elevation plate 22. The blocker rod 140 may also have a quick connect proximal end which can be attached to a handle to aid in threaded coupling to the receptacle 28. To differentiate the blocker rod 140 and the guide rod 50, the blocker rod 140 may be shorter than the guide rod 50 and/or may be of different color than the guide rod 50. An elevator plate retainer 142 (FIG. 21) may be employed to prevent the elevator plate 22 from lifting off the base plate 18 during implantation of the base assembly 12. The elevator plate retainer 142 includes a cannulated shaft 143, dimensioned to pass over the guide rod 50, and a head 144 including an elongate extension that sits above base plate 18 and elevator plate 22 to prevent the elevator plate 22 from moving. At step 122, the elevator plate retainer is introduced over the guide rod 50 until the elongate extension of the head 1844 passes into the slot 36 in the support strut 20. With the elevator plate 22 secure, the implant base assembly 12 is inserted into the T-cut cavity 117 (step 124), as shown in FIG. 22.

FIGS. 23A and 23B illustrate a pair of example embodiments of blocker 146. The blocker 146 includes a blocker plate 148 situated at the distal end of a cannulated shaft 147. The blocker plate 148 includes a cutout region 149 that facilitates slidable insertion of distraction shims and the support column 14 past the blocker plate 148 and into the base plate assembly 12. A set screw 152 encroaches into the cannulation 150 of the shaft 147 to secure the blocker 146 to the blocker rod 140, which in turn is secured to the base plate 18 (thus preventing the base assembly 12 from further advancement). The blocker shown in FIG. 23A has a metallic (e.g. titanium) mesh blocker plate that provides a large footprint for maximum contact with the vertebral body. The blocker shown in FIG. 23B includes a polymer (e.g. PEEK) blocker plate with a small (and radiolucent) foot print maximum visualization. At step 126, illustrated in FIG. 24, the blocker 146 is introduced over the blocker rod 140 until the blocker plate 148 contacts the vertebral body 52. The blocker 146 is then secured to the blocker rod 140 with the set screw 152.

Figure 27:
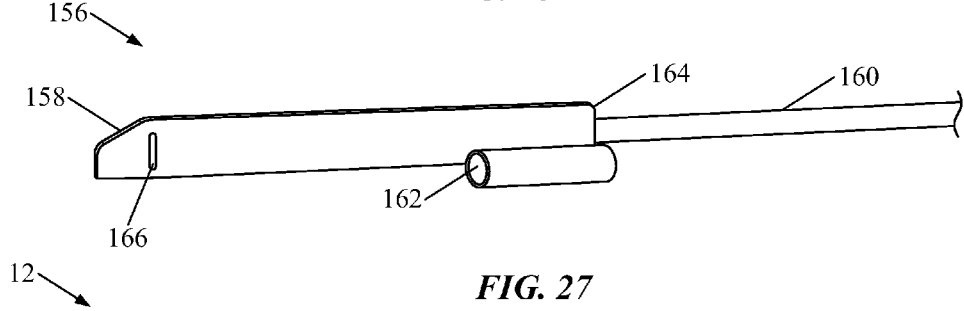
FIG. 27 is a perspective view of a shim for elevating the elevator plate above the base assembly, according to one example embodiment.
Figure 28:
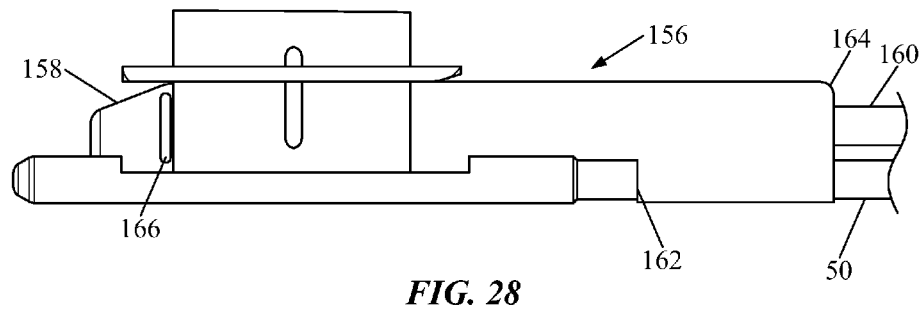
FIG. 28 is a side view of a the shim of FIG. 27 inserted into the base assembly.
Figure 29:
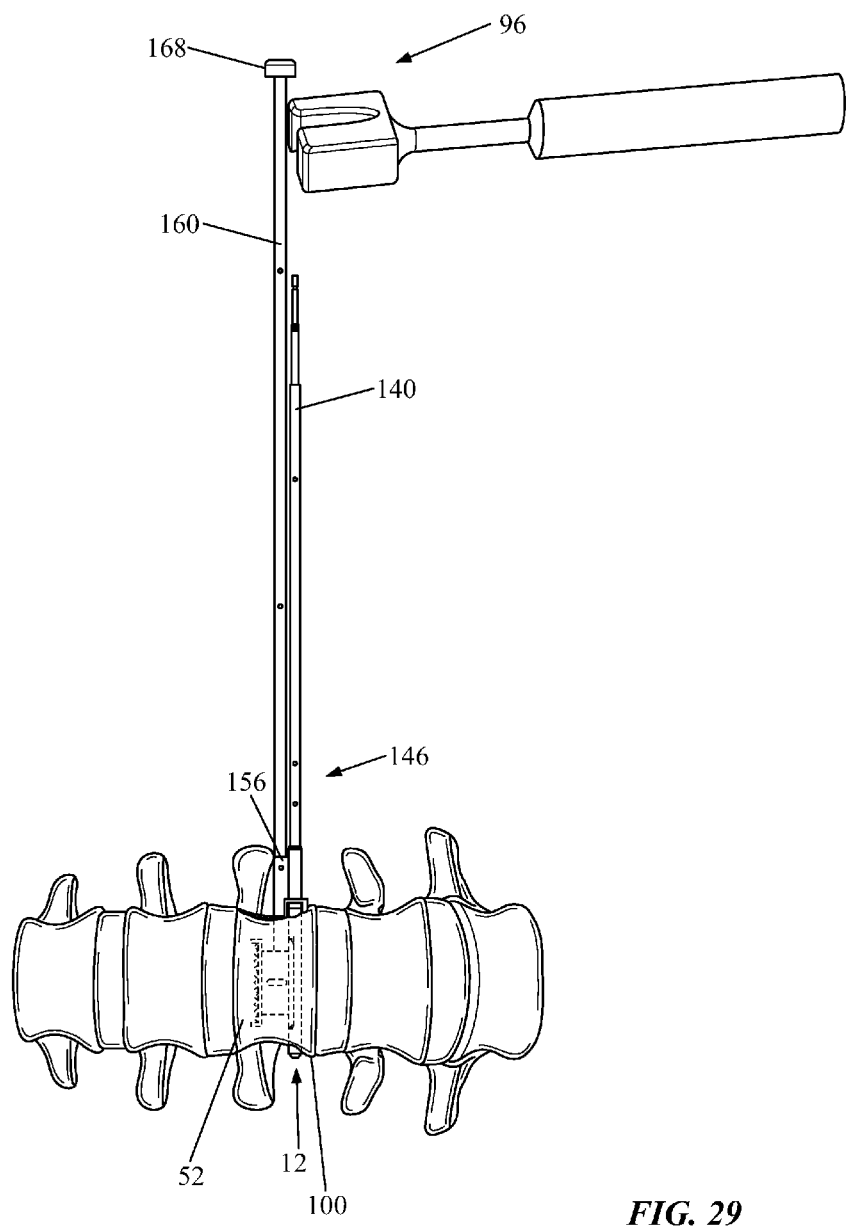
FIG. 29 is an anterior view of a spine with a shim inserted into the base assembly implanted in the vertebral body.
Figure 30A:
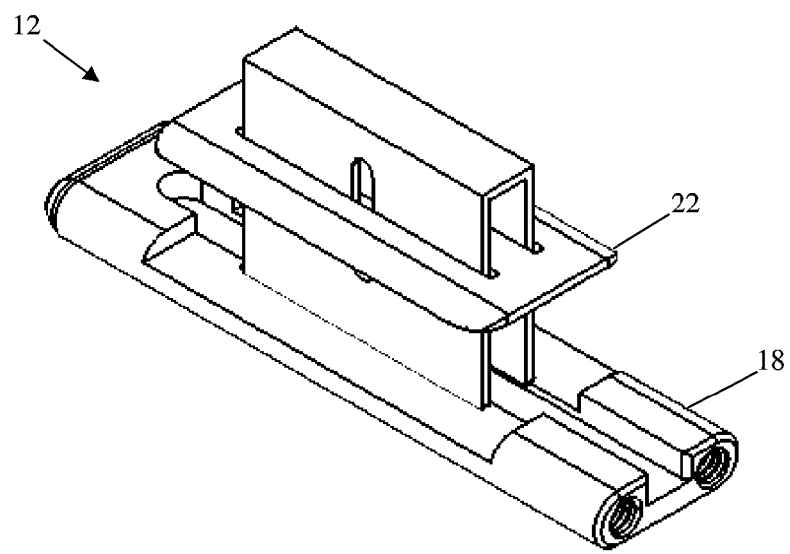
FIG. 30A is a perspective view of the base assembly of FIG. 3 with the elevator plate in a partially elevated position.
Figure 30B:
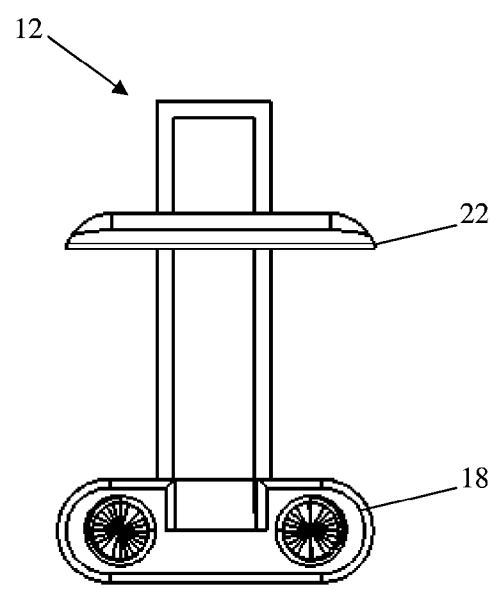
FIG. 30B is a proximal view of the base assembly of FIG. 3 with the elevator plate in a partially elevated position.
Figure 31A:
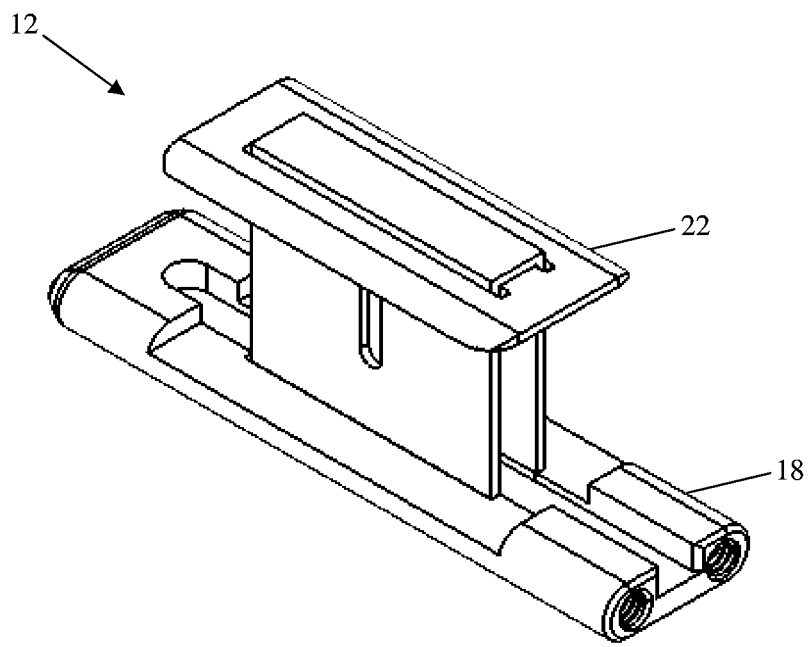
FIG. 31A is a perspective view of the base assembly of FIG. 3 with the elevator plate in a fully elevated position.
Figure 31B:
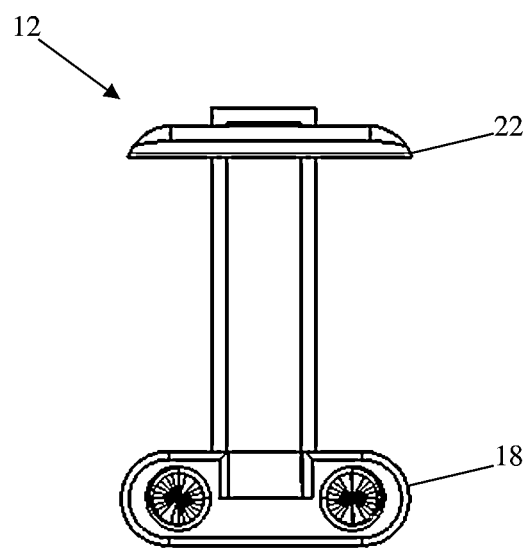
FIG. 31B is a proximal view of the base assembly of FIG. 3 with the elevator plate in a fully elevated position.
Figure 32:
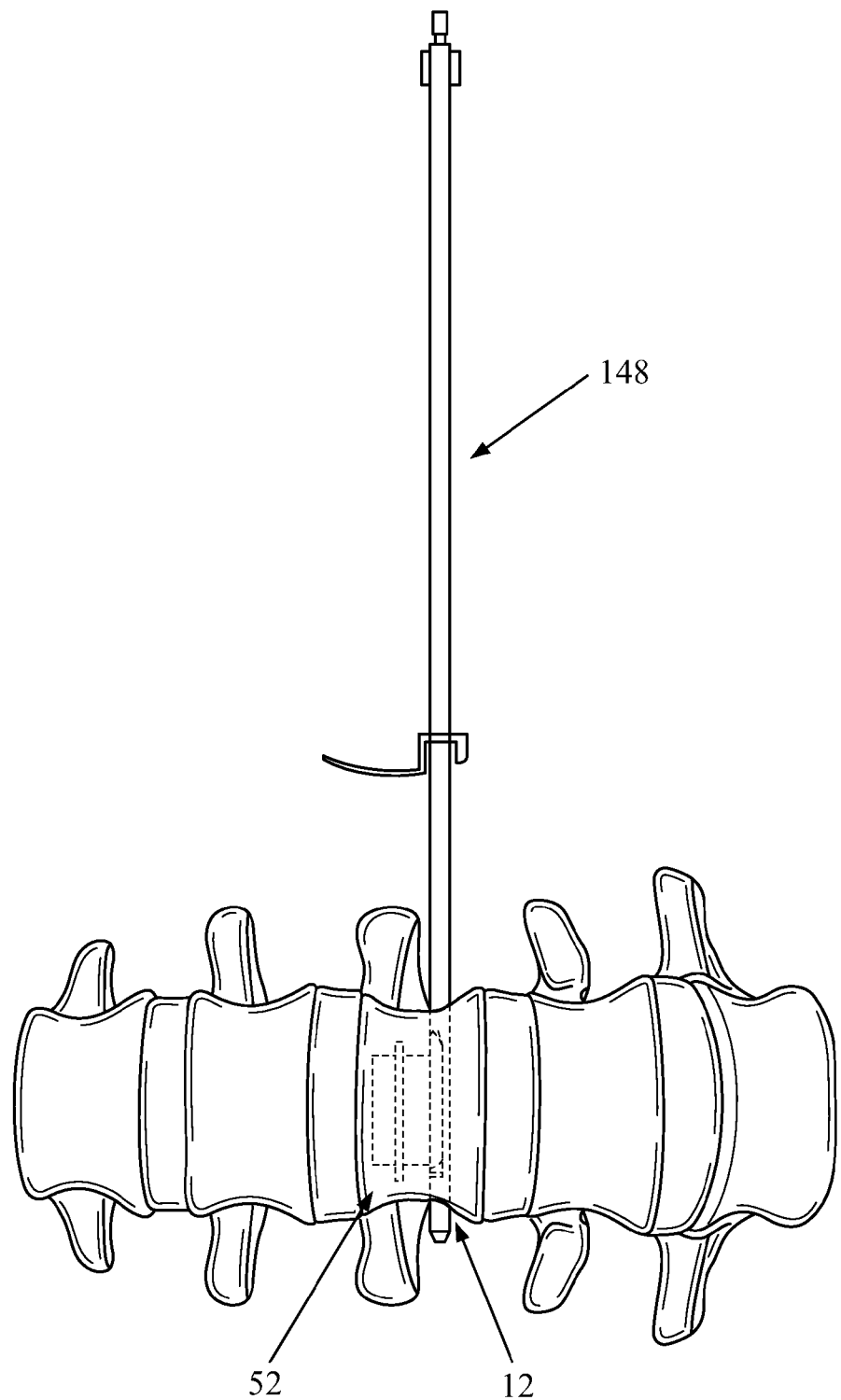
FIG. 32 is an anterior view of the spine of FIG. 26 with the blocking plate being removed after the elevator plate has reached the appropriate elevated position.

At step 130, a plurality of shims 156 are successively inserted to raise the elevator plate 22 to the selected height. With reference to FIG. 27, the distraction shims 156 have a tapered distal end 158 that facilitates lifting of the elevator plate 22 as the shim is inserted down the longitudinal channel 37 and through the slot 36 in the support strut 20. A guide tube 162 along the side of the shim 156 is dimensioned to permit passage of the guide rod 52 such that the shim is easily guided into and along the channel 37 and slot 36. A shaft 160 extends proximally from the shim 156 to facilitate insertion of the shim. The end of the shaft 160 includes a knob 168 that facilitates removal of the shim (for example using the forked mallet 96. A viewing slot 166 situated near the distal end of the shim is viewable under A/P fluoroscopy to monitor shim advancement. As a first (smallest) shim 156 is inserted, the elevator plate 22 is lifted upward such that the cancellous bone above it is compressed toward the cortical endplate. The shim 156 is advanced until the view slot 166 is viewable past the distal end of the support strut 20. The small shim 156 may then be removed and a second larger shim 156 may be inserted such that the elevator plate 22 is lifted further upward compressing the cancellous bone and lifting the cortical endplate. FIGS. 30A-B depict the base plate 18 and elevator plate 22 after partial elevation of the elevator plate 22. Insertion of sequentially larger shims 156 continues until the elevator plate is fully raised to the selected height. With the elevator plate 22 raised to the final position, the blocker plate 146 and blocker rod 140 are removed (step 132) in preparation for insertion of the support column.

Figure 33:
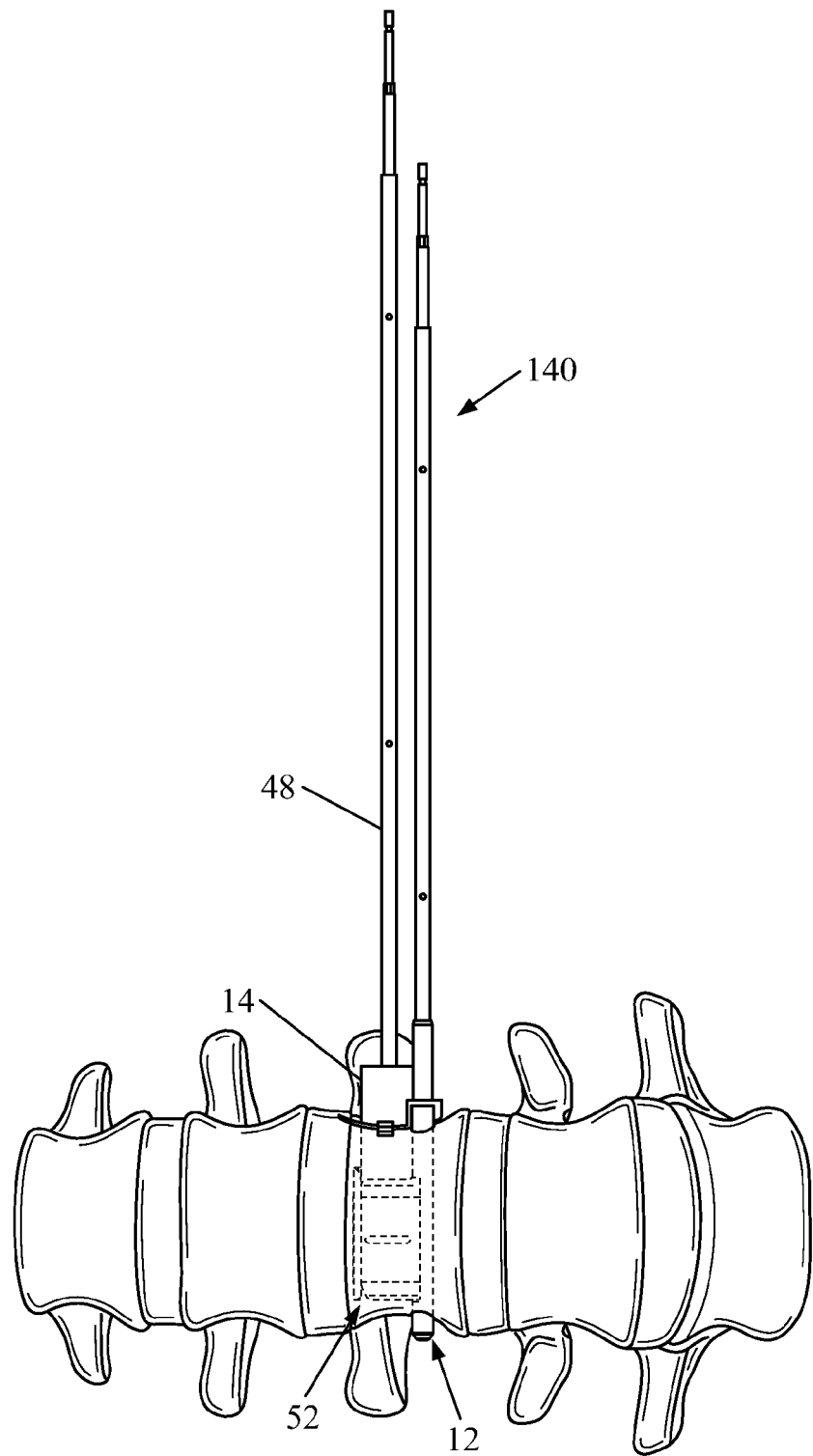
FIG. 33 is an anterior view of the spine of FIG. 26 blocker removed and the support column being inserted into the base assembly.
Figure 34:
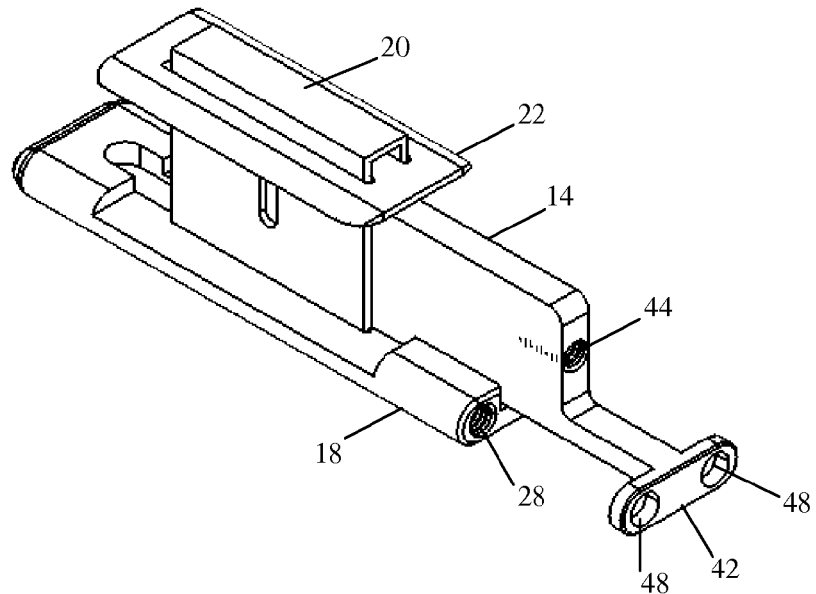
FIG. 34 is a perspective view of the implant assembly of FIG. 1 with the elevator plate fully raised and the support column being inserted.
Figure 38:
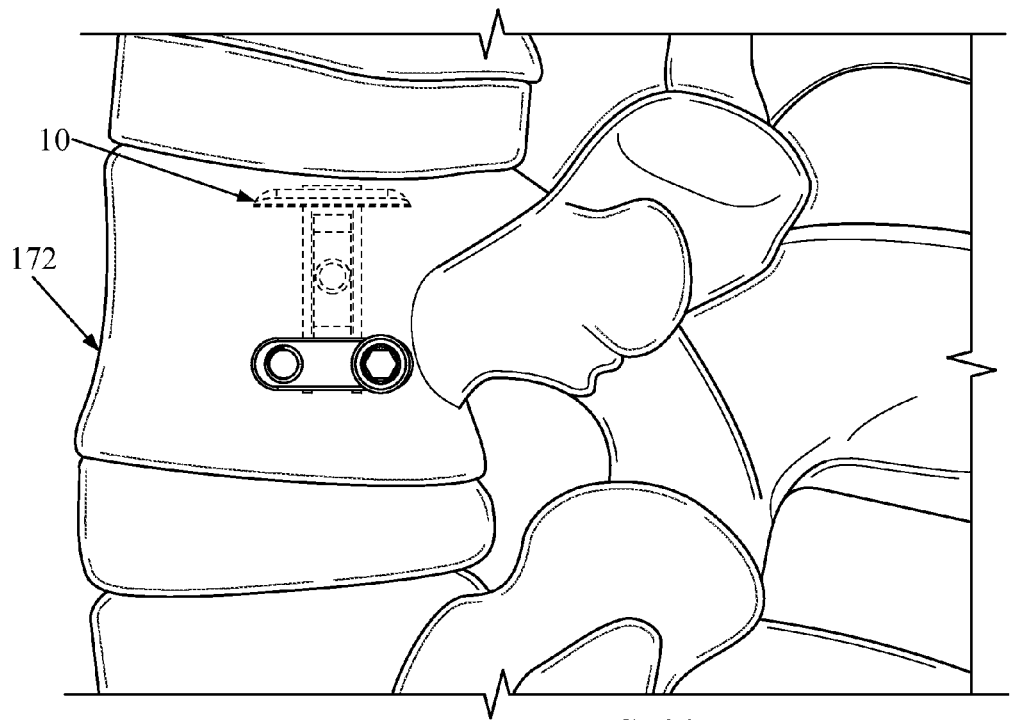
FIG. 38 is an anterior view of a spine with the implant assembly of FIG. 1 implanted in the target vertebral body.
Figure 39:
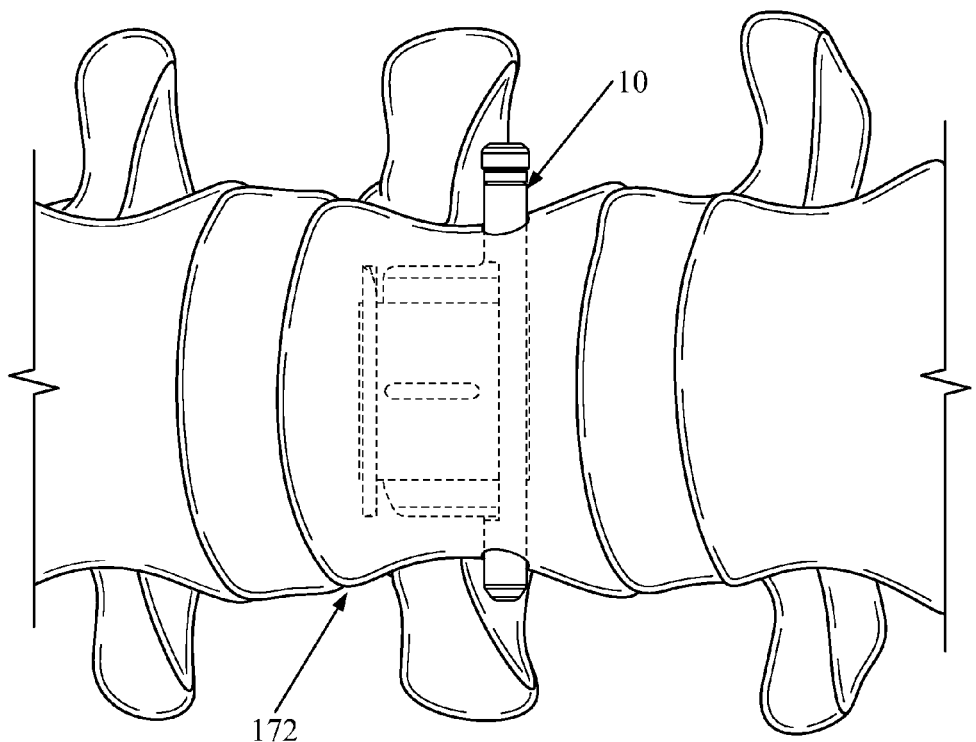
FIG. 39 is a lateral view of a spine with the implant assembly of FIG. 1 implanted in the target vertebral body.

At step 134, the support column 14 is inserted into the base plate assembly 14 as shown in FIGS. 33-35. To accomplish this, the support column 14 is coupled to the support column inserter 54 which is threaded into the hole 43 in the body 40 of the support column. The support column inserter 54 may have a quick connect proximal end which can be attached to a handle to aid in threaded coupling to the hole 43. A guide hole 46 of the support column end face 45 is advanced over the guide rod 52 in order to guide the support column into position. The support column 14 is advanced through the longitudinal channel 37 and slot 36 until the end face 45 rests flush against the distal end 28 of the base plate 20. A locking screw 16 is then passed through the second guide hole 46 with a screw driver 170 (having a length greater than the guide rod 52 and support column insertion rod 54 such that it is not interfered with) and secured into the open receptacle 28 of base plate to secure the support column (step 136). The guide rod 52 and support column inserter 54 are then removed, and if desired, a second locking screw 16 may be secured into the open receptacle 28 through the now open guide hole 46. FIGS. 38-39 show the final implantation configuration of the implant 10 in the reduced vertebra 172. Materials such as bone growth promoting materials or cement may be packed into the void created by the elevation of the elevation plate 22.

While the invention is susceptible to various modifications and alternative forms, specific embodiments thereof have been described herein and shown drawings by way of example in the. It should be understood, however, that the description herein of specific embodiments is not intended to limit the invention to the particular forms disclosed, but on the contrary, the invention is to cover all modifications, equivalents and alternatives falling within the spirit and cope of the invention as defined by the e appended claims. By way of example, it should be appreciated that while the present embodiment includes a single support strut, it is contemplated that more than one (for example, anywhere from two to six) support struts could be used. It is further contemplated that the footprint of the base plate and/or elevator plate may be oval or D-shaped.

What is claimed is:

1. A method for treating a compression fracture of a vertebral body, comprising the steps of:
   forming a T-shaped cavity in the vertebral body;
   coupling a one rod extension to a proximal end of an implant;
   advancing the implant into the cavity in the vertebral body, the implant having a base and an elevation platform, configured in an insertion configuration that matches the T-shaped cavity in the vertebral body;
   elevating the elevation platform by inserting a distraction shim;
   removing the distraction shim;
   guiding a support structure along the rod extension and into position between the base and the elevation platform;
   coupling a second rod extension to a proximal end of the implant;
   advancing a cannulated shaft of a blocking instrument to the vertebral body over the second rod extension; and
   securing the cannulated shaft of the blocking instrument to the second rod extension with a set screw;
   wherein the blocking instrument is secured relative to the implant prior to insertion of the distraction shim.

2. The method of claim 1, wherein elevating the platform by inserting a distraction shim includes sequentially inserting a plurality of shims of increasing height until the desired elevation is achieved.

3. The method of claim 2, wherein the plurality of distraction shims are guided along the rod extension during advancement.

4. The method of claim 1, further including engaging a retaining instrument with the elevation platform and retaining the elevation platform against the base during advancement of the implant into the vertebral body.

5. The method of claim 4, wherein the retaining instrument is guided along the rod extension during advancement.

6. The method of claim 4, wherein the retaining instrument includes a cannulated shaft that passes over the rod extension.

7. The method of claim 1, wherein the second rod extension is coupled to the proximal end of the implant prior to advancing the implant into the vertebral body.

8. The method of claim 1, further including removing the blocking instrument and the second rod extension prior to advancing the support structure into position between the base and the elevation platform.

9. The method of claim 8, further including inserting a lock screw through a hole in the support structure and into a receptacle vacated by removal of the second rod extension to lock the support structure to the implant base.

10. The method of claim 1, wherein said step of forming a T-shaped cavity includes making a first horizontal cut near an inferior portion of the vertebral body and making a second vertical cut in the center of the horizontal cut.

11. The method of claim 10, wherein a location of said first horizontal cut and said second vertical cut is directed by a cutter template.

12. The method of claim 11, further including docking the cutter template to the vertebral body where the horizontal and vertical cuts are to be made and inserting a guide wire into the vertebral body through the cutter template.

13. The method of claim 12, further including removing the cutter template and advancing the first horizontal cutter over the guide wire to make the horizontal cut.

14. The method of claim 13, further including removing the horizontal cutter and advancing a vertical cutter to make the vertical cut.

15. The method of claim 14, wherein a horizontal base of the vertical cutter is guided into the horizontal cut to guide placement of the vertical cut.

\* \* \* \* \*